(12) United States Patent
Laville et al.

(10) Patent No.: US 10,555,894 B2
(45) Date of Patent: Feb. 11, 2020

(54) PLANT EXTRACT COMPRISING SUCROSE ESTERS AS AN ACTIVE AGENT FOR USE IN COSMETIC, DERMATOLOGICAL OR NUTRICOSMETIC COMPOSITION

(71) Applicant: COSMO INTERNATIONAL INGREDIENTS, Mougins (FR)

(72) Inventors: Remi Laville, Drap (FR); Esmeralda Cicchetti, Grasse (FR); Sebastien Garnier, Le Rouret (FR); Leslie Duroure, Grasse (FR); Gerard Manzone, Saint Vallier de Thiey (FR); Jeremie Borsotto, Pegomas (FR)

(73) Assignee: COSMO INTERNATIONAL INGREDIENTS, Mougins (FR)

( * ) Notice: Subject to any disclaimer, the term of this patent is extended or adjusted under 35 U.S.C. 154(b) by 503 days.

(21) Appl. No.: 15/110,215

(22) PCT Filed: Jan. 9, 2015

(86) PCT No.: PCT/FR2015/000011
§ 371 (c)(1),
(2) Date: Jul. 7, 2016

(87) PCT Pub. No.: WO2015/104484
PCT Pub. Date: Jul. 16, 2015

(65) Prior Publication Data
US 2016/0331676 A1    Nov. 17, 2016

(30) Foreign Application Priority Data

Jan. 10, 2014  (FR) ...................................... 14 00051

(51) Int. Cl.
| | |
|---|---|
| *A61K 8/97* | (2017.01) |
| *A61K 8/60* | (2006.01) |
| *A61Q 19/00* | (2006.01) |
| *A61Q 19/08* | (2006.01) |
| *A61Q 19/02* | (2006.01) |
| *A61K 36/81* | (2006.01) |
| *A23L 33/105* | (2016.01) |

(52) U.S. Cl.
CPC .............. *A61K 8/97* (2013.01); *A23L 33/105* (2016.08); *A61K 8/60* (2013.01); *A61K 36/81* (2013.01); *A61Q 19/007* (2013.01); *A61Q 19/02* (2013.01); *A61Q 19/08* (2013.01); *A23V 2002/00* (2013.01); *A61K 2236/00* (2013.01)

(58) Field of Classification Search
None
See application file for complete search history.

(56) References Cited

FOREIGN PATENT DOCUMENTS

FR        2896155 A1       7/2007

OTHER PUBLICATIONS

Franco, et al., Biomedica, 27:110 [machine translation]. (Year: 2007).*
Franco, et al., Planta Med, 80:1605. (Year: 2014).*
Chang, et al., AAPS J., 15:41. (Year: 2013).*
Franco, L.A., et al. "Activity 1,2,4-8 , anti-inflammatory extracts and fractions obtained calyx of Physalis peruviana" , Biomedical Journal of the National Institute Health , CO, vol. 27, Jan. 1, 2007, pp. 110-115.
Barrientos, E.M. Talero, et al., "Anti-inflammatory effect of the ether extract and major fraction of Physalis peruviana calyces in acute TNBS-induced colitis", Abstract of the 6th European Congress of pharmacology (EPHAR 2012).
Desai, NB et al., Sucrose esters—an interesting class of substances for cosmetics, Parmfumerie and Cosmetic, Huethig, Heidelberg, DE, vol. 66, No. 10, Jan. 1, 1985, pp. 629-632.
"International Cosmetic Ingredient Dictionary and Handbook, fourteenth edition 2012", vol. 2, p. 2414.
International Preliminary Report on Patentability, (English Translation) Jul. 8, 2016.

* cited by examiner

*Primary Examiner* — Michael Barker
(74) *Attorney, Agent, or Firm* — Tarolli, Sundheim, Covell & Tummino LLP

(57) ABSTRACT

The invention relates to a plant extract from the calyx of one of the many plants of the Solanaceae family, of the *Physalis* genus, comprising mainly one or more moderately polar to non-polar sucrose esters having a carbon number of acyl groups from C1 to C10 for use as an active agent in cosmetic, dermatological or nutracosmetic compositions. It also relates to the purified sucrose esters of the plant extract or the synthesised sucrose esters as described for the same use.
The invention also relates to a cosmetic, dermatological or nutracosmetic composition comprising as active ingredient, a plant extract or the synthesised sucrose esters in a suitable physiological medium.
Finally, it also relates to the preparation method of the said plant extract.

5 Claims, 6 Drawing Sheets

Figure 1A:
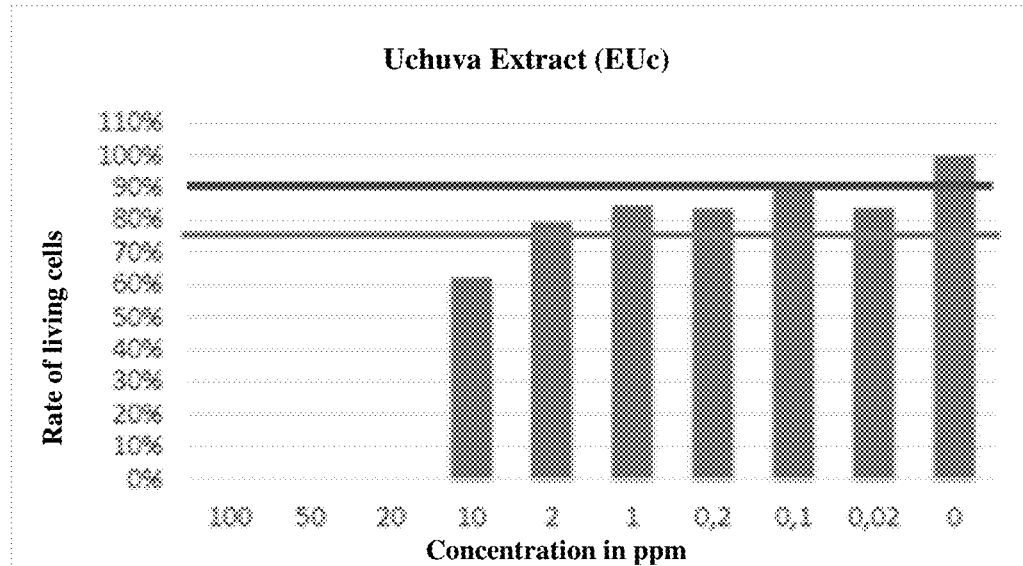

PLANT EXTRACT COMPRISING SUCROSE ESTERS AS AN ACTIVE AGENT FOR USE IN COSMETIC, DERMATOLOGICAL OR NUTRICOSMETIC COMPOSITION

This invention falls in the cosmetic, dermatological and nutracosmetic domain.

It relates to a plant extract from the calyx of one of the many plants of the Solanaceae family, of the *Physalis* genus, comprising mainly one or more moderately polar to non-polar sucrose esters having a carbon number of acyl groups from C1 to C10 for use as an active agent in cosmetic, dermatological or nutracosmetic compositions. It also relates to the purified sucrose esters of the plant extract or the synthesised sucrose esters as described for the same use. It further relates to a cosmetic, dermatological or nutracosmetic composition comprising as active ingredient, a plant extract or the synthesised sucrose esters in a suitable physiological medium. Finally, it also relates to the preparation method of the said plant extract.

The cosmetic, dermatological and nutracosmetic compositions are designed to improve moisturising and the barrier function of the epidermis, promote healing, depigment the skin, and fight against skin ageing in a preventive and/or curative manner.

Skin is a vital organ, composed of several layers (dermis, proliferative layers and *stratum corneum*), that covers the entire body surface and essentially acts as a barrier against the external environment. This barrier function is particularly based on the quality of the epidermis which mainly depends on the condition of the stratum corneum and the balance between the proliferation and differentiation of the epidermal keratinocytes.

The keratinocytes are cells that constitute 90% of the superficial layer of the skin (epidermis) and skin appendages (nails, hair, body hair). They synthesise keratin, a water-insoluble fibrous protein, which gives skin its impermeability and external protection. The epidermis is divided into four layers based on the morphology of the keratinocytes, which gradually move from the basal layers to the upper layers by cellular differentiation till the stratum corneum where they form a layer of dead cells called squamas, by apoptosis. This layer forms a protective barrier and reduces water loss from the organism. The keratinocytes are constantly renewed. It takes them approximately one month to move from the basal layer to the stratum corneum, but this process can be accelerated in case of hyperproliferation of keratinocytes (psoriasis).

The modulation of the differentiation of the keratinocytes is a biological process that can occur in the treatment of the manifestations of skin ageing, be it in the barrier function of the skin or formation of wrinkles. The retinoides (retinol, retinoic acid among others), recognised as cosmetic and dermatological active ingredients that act against several skin problems like psoriasis, acne and wrinkles[21,22], are also an active inhibiting the differentiation of keratinocytes. However, they cause inflammation of the skin prompting research laboratories to look for new retinoide-like actives inhibiting the differentiation of the keratinocytes that are non-inflammatory.[23]

Fibroblasts are cells present in the connective tissue, and are sometimes called supporting cells. These cells are mainly found in the dermis giving it its consistency and suppleness. They secrete proteoglycans and glycoproteins. They mainly secrete collagen, elastin and fibrillins, including fibrillin 1.

Fibrillin 1 is a glycoprotein that belongs to a protein family with three members whose regulation is still a mystery. It is secreted by fibroblasts as well as keratinocytes. It constitutes the major element of the microfibrils in elastic and non-elastic extracellular matrices. Fibrillin 1 thus contributes to the formation of fibres and their functional and structural properties play an essential role in the elasticity of the connective tissue, especially at the level of the dermo-epidermal junction. In fact, it enables the epidermal cells to be attached to the elastic fibres of the dermis.

At the level of the dermis, it is observed that with age there is a decrease in the activity of the fibroblasts along with a decrease in their proliferation, biosynthesis and exchanges with the extracellular matrix, as well as a qualitative and quantitative deterioration of the support fibres.

A flattening appears at the level of the dermo-epidermal junction which leads to a decrease in the cohesion between these two areas (dermis and epidermis), with rarefaction of the elements of the dermis as well as anchoring fibres, which leads to a decrease in the metabolic exchanges and formation of wrinkles. Striae atrophicae are caused by very intense stretching of the skin that happens too quickly, which damages the fibroblastic cells associated with a predominant alteration of the collagenic tissue and structural glycoproteins. The formation of striae atrophicae seems to be a modification of the metabolism of the fibroblasts leading to poor healing as well as a loss of contact between the cells and the matrix as stated in patent WO 2001007006[20].

Along with elastin, fibrillin 1 is sometimes mentioned as a protein involved in the processes of firmness and elasticity[9,10], active in the anti-ageing[11, 12, 13, 14, 15] mechanism, and is mainly used as a biomarker of the acceleration of ageing due to ultra-violet[16,17,18] rays, and/or for the treatment of certain cicatricial processes like for striae atrophicae. Thus, the activation of the synthesis of fibrillin 1 could help to treat skin that has aged intrinsically, i.e. genetically programmed or chronological, or extrinsically, mainly due to oxidative stress like UV radiation, tobacco or pollution and to treat scar formation.

The fibroblasts and keratinocytes thus play a crucial role in the biological process of the skin, mainly through the secretion of fibrillin 1, to regulate firmness, elasticity, cellular cohesion and in the process of scarring and ageing of the skin.

Skin becomes dry as it ages. Thus, elderly subjects, especially those more than fifty years old, very often show the manifestation of xerosis or dryness of the mucous membranes, related to lesser secretion of sebum, hormonal changes or slowing down of the hydric flow through the epidermis. The skin then feels itchy and stretched—the two classic symptoms of dry skin. Among the acquired conditions resulting in dry skin are xerosis induced by photochemotherapy and eczema. Among the acquired conditions causing dry mouth, also called xerostomia, are Sjögren's syndrome or radiation therapy to the neck. Finally, among the conditions that involve a dryness of the mucous membranes are ocular and vaginal dryness.

Generally, topical products are used to restore the cutaneous barrier to tackle these problems of skin dryness and ageing. These would include humectants, film-forming agents, retinoid-type molecules and agents that can rebuild the cutaneous barrier, for example squalene.

This invention mainly constitutes the discovery that a certain category of sucrose esters, that are present in certain plant extracts, or synthesised, exhibit interesting biochemical and biological activities on the skin, skin appendages and mucous membranes mainly to improve moisturising, the barrier function of the epidermis, and to prevent and/or combat the signs of skin ageing.

Sucrose esters are acylesters of one or more acyl groups with a carbon number that is more or less significant (e.g. C1 to C22) and a sugar. The sugar is generally sucrose, hence the term sucrose esters or sucroesters. Sucrose esters have an amphiphilic quality that can be modulated according to the degree of esterification of the sugar and the nature of the acyl groups.

They also provide an alternative solution to the industries of the sector of surface-active agents owing to their numerous advantages like their harmlessness, the absence of taste and smell and their non-ionic quality. Sucrose esters have a wide range of applications as surface-active agents like in the field of food-processing, detergents, cosmetics and pharmaceuticals.

The sucrose esters in the market are mainly synthetic and avenues of biosynthesis are increasingly developed to obtain a technique that is eco-responsible and product that is completely natural.[1,2] Natural sucrose esters do exist but are undervalued by the industrial sector. In fact, the family of the Solanaceae, whose most well-known representatives are *Nicotiana tabacum*(tobacco) and *Solanum lycopersicum* (tomato), are known to synthesise and store sucrose esters in their trichomes, as a defense mechanism against potential predators.[3,4]

In the context of looking for natural sucrose esters, research laboratories wondered about the use of such molecules as therapeutic actives. Sucrose esters have biological activities like being anti-bacterial, anti-inflammatory, anti-parasitic, and can modulate the drug multi-resistance.[5,6] As compared to synthetic sucrose esters, the acyl groups of natural sucrose esters can also be aromatic (benzoate, etc.).[7] There is a lot of medicinal chemistry research on these aromatic sucrose esters as anti-tumour agents.[8]

The EP 0 280 413 document describes the use of sucrose esters to increase the penetration of biological actives through the skin. These sucrose esters, obtained by synthesis, are sucrose monolaurate or alternately the mixture of the sucrose of coconut fatty acids in which the predominant fatty acid is lauric acid (C12).

The JP61271205 document describes that certain synthetic glucose-esters with very long chains (more than 22 carbons), in combination with glycosylceramide or ceramide, are useful to increase the wettability, suppleness and elasticity of the skin.

The JP 2001 122731 document describes that a plant extract, without indicating the plant or the part of the plant, is useful in cosmetics to treat skin dryness and as a detergent. The solvents mentioned to obtain the extraction are essentially polar and thus lead to the extraction of polar molecules.

The JP 2011 051920 document describes the use of a *Physalis peruviana* extract to lighten skin and reduce age spots. This document discusses the use of the fruit of *Physalis peruviana*.

The document of Franco L A et al., "Actividad antiinflammatoria de extractos y fracciones obtenidas de calices de *Physalis peruviana* L", Biomedica, vol. 27, 1 Jan. 2007, reveals an extraction process of an extract from the calyx of *Physalis peruviana* to develop an anti-inflammatory activity of the said extract.

The document of E. M Taleo Barrientos et al., "Anti-inflammatory effect of the ether extract and major fraction of *Physalis peruviana* calyces in acute TNBS-induced colitis", Abstract of the 6th European Congress of pharmacology, 2012, reveals an extraction process of an extract from the calyx of *Physalis peruviana* to demonstrate that two new sucrose esters exhibit an anti-inflammatory activity at the level of the colon.

The FR 2 896 155 document reveals the use of the *Physalis* extract, mainly alkenkegi, in the cosmetics domain to combat ageing. The extraction process of the active molecules is a polar and hydrophilic extraction and the extracted molecules are thus polar, mainly the polyphenols, withanolides and sugars.

The document of Desai N B et al., "Sucrose esters—an interesting class of substances for cosmetics", *Parfumerie and kosmetik, Huethig, Heidelberg, D E*, vol. 66, No. 10, 1 Jan. 1985, reveals synthetic sucrose esters that are valuable for cosmetics. Table 1 describes sucrose esters with a carbon number of the acyl groups from C12 to C18. These sucrose esters are considered to have a moisturising, smoothing and anti-irritant activity and help obtaining non-irritating cleansers in the cosmetics and pharmaceutical fields.

In addition to their therapeutic and surface-active property mainly anti-bacterial, anti-inflammatory and antiparasitic, the moderately polar to non-polar sucrose esters with a carbon number of the acyl groups from C1 to C10 have never been described as having any cosmetic, dermatological or nutracosmetic activity for the skin, mucous membranes or skin appendages.

The inventers have especially highlighted that certain moderately polar to non-polar sucrose esters from plant extract have a biological activity on the activation of fibrillin 1 and the inhibition of the differentiation of the keratinocytes in particular. The said sucrose esters have also surprisingly shown a biological activity on several biological targets such as collagen I, III and IV, elastin, fibrillin-1, involucrin, melanin and filaggrin.

Thus, the inventors of this invention have surprisingly highlighted a new plant-based active ingredient that can activate several biological targets related to ageing, moisturising and depigmentation. The inventors have mainly featured a new plant-based active ingredient that can activate the synthesis of fibrillin 1 by fibroblasts and keratinocytes and/or inhibit the differentiation of the keratinocytes and biologically act on several biological targets like collagen I, III and IV, elastin, fibrillin-1, involucrin, melanin and filaggrin, and thus improve the appearance of the skin, mucous membranes and skin appendages, prevent and/or fight against the manifestations of intrinsic and/or extrinsic skin ageing, aid the process of healing especially in the case of striae atrophicae, prevent and/or combat dryness of the skin, mucous membranes and/or skin appendages and depigment skin.

In this invention,
"effective quantity of active ingredient" is understood to mean the required quantity of the active molecules to obtain the result sought, that is to say, to enable obtaining a biological activity on the skin, the skin appendages and/or mucous membranes. For this invention, it will be understood as "effective quantity of plant extract" or "effective quantity of sucrose esters" given that the plant extract of the invention mainly constitutes sucrose esters as the active ingredient.

"active ingredient" is understood to mean one or more of the sucrose esters or plant extract mainly comprising one or more of the sucrose esters.

"topical application" refers to applying or spreading the active ingredient of the invention, or a composition containing it, on the surface of the skin, a mucous membrane or skin appendages.

"cosmetically or dermatologically acceptable" is understood to mean that the active ingredient in the invention, or a composition containing it, is suitable to come in contact with skin or a mucous membrane without triggering any allergic or toxic reactions.

"physiologically suitable or acceptable" is understood to mean that the compositions are suitable for topical or transdermal use, in contact with the mucous membranes, skin appendages (nails, hair, body hair), scalp and mammal and more specifically human skin as the compositions can be ingested or injected into the skin, without any risk of toxicity, incompatibility, instability and allergic response.

"physiologically suitable or appropriate medium" or "appropriate excipient" is understood to mean, without being limited to, a hydroalcoholic or aqueous solution, a water-in-oil emulsion, an oil-in-water emulsion, a microemulsion, an aqueous gel, an anhydrous gel, serum, dispersion of vesicles, powder. This physiologically acceptable environment forms what is conventionally called the excipient of the composition.

"active biologically" refers to "something that possesses an in vivo or in vitro activity which is characteristic of the activity of the active ingredient of the invention".

"cutaneous manifestations of ageing" are understood to mean all modifications of the exterior appearance of the skin and the appendages due to ageing, such as, wrinkles and fine lines, withered skin, flabby skin, thinned skin, the lack of elasticity and/or tonus of the skin, dull skin without brightness, or pigmentation blemishes of the skin, hair discoloration or spots on nails, as well as any internal modification of the skin that does not systematically manifest in a modified exterior appearance like, for example, any internal deterioration of the skin after exposure to ultraviolet (UV) radiation.

"mainly comprises" is understood to mean that the sucrose esters obtained by extraction of a plant matrix are predominantly present in the plant extract, i.e. more than 50% by weight, preferably more than 80%, and still more preferably from 90% to 100%.

"synthesised sucrose esters" is understood to mean any manner of obtaining sucrose esters, by hemisynthesis or synthesis, whether by chemical, biochemical or biotechnological synthesis.

A first object of the invention is the plant extract from the calyx of one of the many plants of the Solanaceae family, of the *Physalis* genus, comprising mainly one or more moderately polar to non-polar sucrose esters having a carbon number of acyl groups from C1 to C10 for use as an active ingredient that is biologically active on skin, skin appendages and mucous membranes.

Preferentially, the invention comprises the plant extract from the calyx of one of the many plants of the Solanaceae family, of the *Physalis* genus, comprising mainly one or more moderately polar to non-polar sucrose esters having a carbon number of acyl groups from C1 to C10 for use as an active ingredient that is biologically active on skin, skin appendages and mucous membranes, with the exception of anti-inflammatory activity.

This biological activity is specifically to improve the appearance of the skin, mucous membranes and skin appendages, prevent and/or fight against the manifestations of intrinsic and/or extrinsic skin ageing, aid the process of healing especially in the case of striae atrophicae, prevent and/or combat dryness of the skin, mucous membranes and/or skin appendages and depigment the skin.

In a preferred embodiment, one or more moderately polar to non-polar sucrose esters having a carbon number of acyl groups from C1 to C10 has/have the following generic formula:

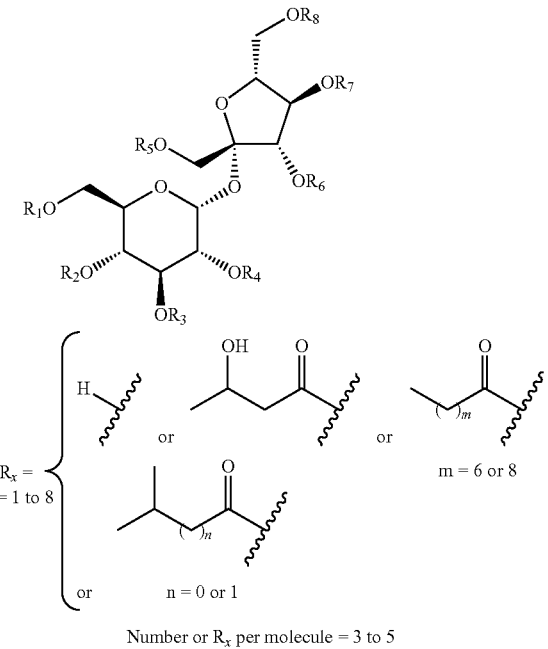

The moderately polar to non-polar sucrose esters having a carbon number of acyl groups from C1 to C10 as described in the generic formula are present in the plant extract up to 50% to 100% by weight of the total extract, preferably from 80% to 100% by weight of the total extract and still more preferably 100% by weight of the total extract. These quantities are based on examples 1, 2 and 3 that enabled testing the biological activity of sucrose esters present in the plant extract of the invention.

As shown in the examples below, it is possible to obtain a plant extract comprising 80% to 100% moderately polar to non-polar sucrose esters having a carbon number of acyl groups from C1 to C10. It is also possible to separate the different sucrose esters obtained to obtain a purified extract from single sucrose ester as described above.

In a preferred embodiment of the invention, the plant extract comprises one or more of the following sucrose esters:

the 3-O-(2-methyl-1-oxopropyl)-β-D-fructofuranosyl (1→2)-3,4-bis(2-methylpropanoate)-2-decanoate-α-D-glucopyranoside, the 3-O-(3-methyl-1-oxobutyl)-β-D-fructofuranosyl(1→2)-3,4-bis(2-methylpropanoate)-2-decanoate-α-D-glucopyranoside, the 3-O-(3-methyl-1-oxobutyl)-β-D-fructofuranosyl(1→2)-3-(2-methylpropanoate)-2-decanoate-α-D-glucopyranoside, the 3-O-(2-methyl-1-oxopropyl)-β-D-fructofuranosyl (1→2)-3,6-bis(2-methylpropanoate)-2-decanoate-α-D-glucopyranoside, the 3-O-(2-methyl-1-oxopropyl)-β-D-fructofuranosyl (1→2)-3-(3-methylbutanoate)-2-decanoate-α-D-glucopyranoside, the 3-O-(2-methyl-1-oxopropyl)-β-D-fructofuranosyl (1→2)-3,4-bis(2-methylpropanoate)-2-nonanoate-α-D-glucopyranoside, the 3-O-(2-methyl-1-oxopropyl)-β-D-fructofuranosyl(1→2)-3,4-bis(2-methylpropanoate)-2-octanoate-α-D-glucopyranoside.

In an even more preferred embodiment of the invention, the plant extract comprises one or more of the following sucrose esters:
the 3-O-(2-methyl-1-oxopropyl)β-D-fructofuranosyl(1→2)-3,4-bis(2-methyl pro-panoate)-2-decanoate-α-D-glucopyranoside,
the 3-O-(3-methyl-1-oxobutyl)β-D-fructofuranosyl(1→2)-3,4-bis(2-methylpropa-noate)-2-decanoate-α-D-glucopyranoside.

In a preferred embodiment of the invention, the plant extract comes from the calyx of *Physalis peruviana*.

A second object of the invention concerns moderately polar to non-polar sucrose esters having a carbon number of acyl groups from C1 to C10 obtained from plant extract of the invention or synthesised, for use as an active ingredient that is biologically active on skin, skin appendages and mucous membranes.

In a preferred embodiment, the invention concerns moderately polar to non-polar sucrose esters having a carbon number of acyl groups from C1 to C10 obtained from plant extract of the invention or synthesised, for use as an active ingredient that is biologically active on skin, skin appendages and mucous membranes, with the exception of anti-inflammatory activity.

In a preferred embodiment, the moderately polar to non-polar sucrose esters having a carbon number of acyl groups from C1 to C10 have the following generic formula:

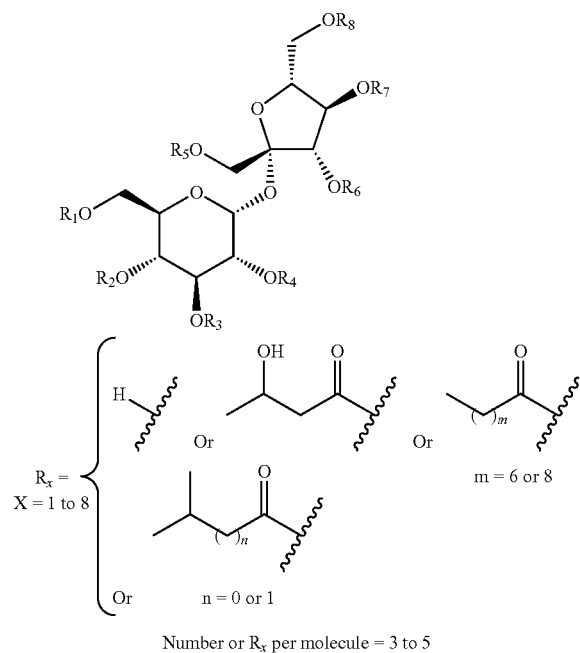

Number or $R_x$ per molecule = 3 to 5

In fact, the moderately polar to non-polar sucrose esters having a carbon number of acyl groups from C1 to C10 that can be used as an active agent in cosmetic, dermatological and nutracosmetic compositions can come:
either from the extraction process from the calyx of one of the many plants of the Solanaceae family, of the *Physalis* genus, thus enabling to obtain an extract that mainly comprises a mixture of moderately polar to non-polar sucrose esters having a carbon number of acyl groups from C1 to C10, or after purification, a quantity of a single moderately polar to non-polar sucrose ester with a carbon number of acyl groups from C1 to C10.
or from the synthesis of one or more of the moderately polar to non-polar sucrose esters with a carbon number of acyl groups from C1 to C10 as described. The person skilled in the art is quite capable of synthesising the sucrose esters individually, by the different known ways, to constitute a sucrose esters-based active ingredient of the invention.

The moderately polar to non-polar sucrose esters with a carbon number of acyl groups from C1 to C10 are acyl esters of one or more acyl groups with a carbon number from C1 to C10 and sucrose.

A third object of the invention concerns a cosmetic, dermatological or nutracosmetic composition comprising as active ingredient, a plant extract of the invention or the synthesised sucrose esters of the invention in a suitable physiological medium.

The composition of the invention can be formulated in the form of different preparations suitable for topical administration, for oral, rectal, vaginal, nasal, auricular or bronchial administration, for parenteral administration.

For the first variant, the different preparations are adapted for topical administration and include creams, emulsions, milks, ointments, lotions, oils, glycolic, hydroalcoholic or aqueous solutions, powders, patches, sprays or any other product meant to be applied externally.

For the second variant, the different preparations are adapted for oral administration. The plant extract comprising the sucrose esters can go through either a food composition or a food supplement. The food supplement can take the form of capsules or plant or gelatine soft capsules in the context of this invention. The said food supplement can contain 0.01% to 100%, by weight, of the plant extract.

For cosmetic or dermatological use, the composition will be best formulated in the form of a preparation that is suitable for topical administration.

For dietary use, for nutritive or cosmetic use (cosmetofood or nutri-cosmetic or nutracosmetic), the composition will be best formulated in the form of a preparation that is suitable for oral administration. It is possible for it to not contain any excipient and to be fully constituted by plant extract mainly comprising sucrose esters or synthesised sucrose esters and corresponding favourably to the generic formula stated above.

The compositions of the invention are more particularly meant to be administered topically. Thus, these compositions should contain a cosmetically and/or dermatologically acceptable medium, i.e. compatible with skin and skin appendages, and covering all the cosmetic or dermatological forms. These compositions can essentially be in the form of creams, oil-in-water or water-in-oil emulsions or multiple emulsions, solutions, suspensions, gels, milks, lotions, sticks or even powders, and suitable to be applied on skin, lips and/or skin appendages. These compositions include the excipients that are necessary for their formulation, like solvents, thickeners, thinners, surface-active agents, antioxidants, colouring agents, preservatives, perfumes. They can be used as health care products and/or make-up products.

The composition of the invention can particularly consist of a composition for hair care, mainly a shampoo, conditioner, a treating lotion, a styling gel or cream, a hair restructuring lotion, mask, etc. The cosmetic composition of the invention can mainly be used in treatments that involve an application that is or is not followed by rinsing, or even in the form of shampoo. The composition of the invention can be effectively used in antidandruff treatments. It can also be in the form of a dye or mascara to be applied with a brush or a comb, especially on the eyelashes, eyebrows or hair.

In addition, the compositions of the invention include any additive that is commonly used in the intended domain of application as well as the additives necessary for their formulation, like solvents, thickeners, thinners, antioxidants, colouring agents, sunscreens, self-tanning agents, pigments, fillers, preservatives, perfumes, odour absorber, pharmaceutical or cosmetic actives, essential oils, vitamins, essential fatty acids, surface-active agents, film-forming polymers, etc.

The INCI Dictionary & Handbook ("International Nomenclature of Cosmetic Ingredients 13th Ed. 2010) published by "Personal Care Products Council, Inc.", Washington, D.C.) describes a non-exhaustive wide variety of cosmetic and pharmaceutical ingredients that are generally used in the skin-care industry and are suitable to be used as additional ingredients in the compositions of this invention.

The non-exhaustive examples of these classes of additional ingredients include: healing agents, anti-ageing agents, anti-wrinkle agents, anti-atrophy agents, moisturising agents, soothing agents, anti-bacterial agents, antiparasitic agents, antifungal agents, fungicidal agents, fungistatic agents, bactericidal agents, bacteriostatic agents, antimicrobial agents, anti-inflammatory agents, anti-pruriginous agents, anaesthetic agents, antiviral agents, keratolytic agents, anti-free radical agents, anti-seborrheic agents, antidandruff agents, agents modulating the differentiation, proliferation or pigmentation of the skin, agents accelerating penetration, desquamative agents, agents stimulating or inhibiting the synthesis of melanin, depigmenting, lightening or bleaching agents, propigmenting agents, self-tanning agents, NO-synthase inhibiting agents, antioxidant agents, agents that trap free radicals and/or atmospheric anti-pollution, anti-glycation agents, firming agents, agents stimulating the synthesis of the dermal or epidermal macromolecules and/or the agents that can prevent or inhibit their deterioration, the agents stimulating collagen synthesis, agents stimulating elastin synthesis, agents stimulating decorin synthesis, agents stimulating laminin synthesis, agents stimulating defensin synthesis, agents stimulating chaperone synthesis, agents stimulating aquaporin synthesis, agents stimulating hyaluronic acid synthesis, agents stimulating the synthesis of lipids and components of the stratum corneum (ceramides, fatty acids, etc.), agents inhibiting collagen degradation, agents inhibiting elastin degradation, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents inhibiting acetylcholinesterase, agents stimulating glycosaminoglycan synthesis, DNA repairing agents, DNA protecting agents, anti-itching agents, agents for the treatment and/or care of sensitive skin, skin refirming agents, anti-stretch mark agents, astringent agents, agents regulating sebum production, dermo-relaxant agents, coadjuvant healing agents, agents stimulating reepithelialisation, coadjuvant reepithelialisation agents, cytokine growth factors, calming agents, anti-inflammatory agents, agents acting on capillary microcirculation and/or circulation, agents stimulating angiogenesis, agents inhibiting vascular permeability, agents acting on cell metabolism, agents designed to improve dermal-epidermal junction, agents inducing hair growth, agents inhibiting or retarding hair growth, muscle-relaxing agents, antipollution and/or anti-radical agents, agents stimulating lipolysis, slimming agents, anti-cellulite agents, agents acting on microcirculation, agents acting on the metabolism of cells, cleaning agents, hair styling agents, hair growth stimulants, sunscreens, total screens, make-up agents, detergents, pharmaceutical products, emulsifying agents, emollients, organic solvents, antiseptic agents, deodorant actives, physiologically acceptable mediums, surfactants, abrasive agents, absorbents, aesthetic components like perfumes, pigments, dyes, colourants and natural colourants, essential oils, sensates, cosmetic astringents, anti-acne agents, anti-caking agents, anti-foaming agents, antioxidants, binders, organic additives, enzymes, enzymatic inhibitors, enzymatic inductors, coenzymes, chelating agents, plant derivatives and vegetable extracts, essential oils, marine extracts, agents obtained from a biofermentation process and/or biotechnology process, mineral salts, cell extracts, sunscreens (mineral or organic ultraviolet-protecting agents that are active against the ultraviolet A and/or B rays), ceramides, peptides, buffering agents, bulking agents, chelating agents, chemical additives, colouring agents, cosmetic biocides, denaturants, medicinal astringents, external analgesics, film-forming agents, like polymers, to intensify the film-forming properties and the substantivity of the composition, quaternary derivatives, agents increasing the substantivity, opacifying agents, pH regulators and adjusters (e.g. triethanolamine), propellants, reducing agents, sequestrants, skin bleaching and/or lightening agents, skin conditioning agents (i.e. humectants, including miscellaneous and occlusive), substances retaining humidity, alpha hydroxy acids, beta hydroxy acids, moisturisers, epidermal hydrolytic enzymes, skin soothing and/or healing agents, skin treating agents, anti-wrinkle agents, agents that can reduce or treat under-eye bags, exfoliating agents, thickeners, softening agents, gelling polymers, vitamins and their derivatives, wetting agents, peeling agents, soothing agents, curative agents of the skin, lignans, preservatives (i.e. phenoxyethanol and parabens), anti-UV agents, cytotoxic agents, anti-neoplastics, viscosity modifiers, non-volatile solvents, pearling agents, anti-perspirant agents, depilatories, vaccine, perfumed water, skin restructuring agent, excipients, fillers, minerals, anti-mycobacterial agents, anti-allergenic agents, H1 or H2 antihistamines, anti-irritants, agents stimulating the immune system, agents inhibiting the immune system, insect repellents, lubricants, pigmenting or colouring agents, hypopigmenting agents, photo stabilising agents, and mixtures thereof, as long as they are physically and chemically compatible with the other ingredients of the composition and especially with the actives of this invention.

In addition, the nature of these additional ingredients should have no adverse effect on the benefits of the actives of the invention. These additional ingredients can be natural or synthetic like for example, plant extracts or resulting from a process of biofermentation. There are additional examples in the INCI Dictionary & Handbook Such additional ingredients can be selected in the group comprising: amino sugars, glucosamine, D-glucosamine, N-acetyl-glucosamine, N-acetyl-D-glucosamine, mannosamine, N-acetyl mannosamine, galactosamine, N-acetyl galactosamine, vitamin B3 and its derivatives, niacinamide, sodium dehydro-acetate, dehydroacetic acid and its salts, phytosterols, comprising salicylic acid, hexamidines, comprising alkanoyl dihydroxyproline, extracts and derivatives of soya, equol, isoflavones, flavonoids, phytantriol, farnesol, geraniol, bisabolol, peptides and their derivatives, di-, tri-, tetra-, penta-, and hexapeptides and their derivatives, lys-thr-thr-lys-ser, palmitoyl-lys-thr-thr-lys-ser, carnosine, comprising N-acyl amino acid, retinoids, retinyl propionate, retinol, retinyl palmitate, retinyl acetate, retinal, retinoic acid, water-soluble vitamins, ascorbates, vitamin C, ascorbyl glucoside, ascorbyl palmitate, magnesium ascorbyl phosphate, sodium ascorbyl phosphate, vitamins and their salts and derivatives, provitamins and their salts and derivatives, ethyl panthenol, vitamin B and its derivatives, vitamin B1, vitamin B2, vitamin B6, vitamin B12, vitamin K and its derivatives, pantothenic acid and its derivatives, pantothenyl ethyl ether, panthenol and its derivatives, ethyl panthenol, dexpanthenol, biotin, amino acids and their salts and derivatives, water-soluble amino acids, asparagine, alanine, indole, glutamic acid, water-insoluble vitamins, vitamin A, vitamin E, vitamin F, vitamin D and its compounds, mono-, di-, and triterpenoids, beta-ionol, cedrol, and their derivatives, water-insoluble amino acids, tyrosine, tryptamine, particulate materials, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate Zn gluconate, piroctone olamine, 3,4,4'-trichloro-carbanilide, triclocarban, Zn pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove essential oil, menthol, camphor, eucalyptus essential oil, eugenol, menthyl lactate, witch hazel distillate, eicosene and vinyl pyrrolidone copolymer, iodopropyl butylcarbamate, a polysaccharide, an essential fatty acid, a salicylate, glycyrrhetinic acid, carotenoids, ceramides and pseudo-ceramides, a complex lipid, oils in general of natural origin like shea butter, apricot oil, evening primrose oil, prune oil, palm oil, monoï oil, kahai oil, hydroquinone, l'HEPES, procysteine, O-octanoyl-6-D-maltose, disodium salt of methylglycinediacetic acid, steroids such as diosgenin and the derivatives of DHEA, the DHEA dehydroepiandrosterone and/or a precursor or chemical or biological derivative, N-ethyloxycarbonyl-4-para-aminophenol, blueberry extracts, phytohormones, *Saccharomyces cerevisiae* yeast extracts, algae extracts, extracts of soya, lupin, maize and/or peas, alverine and its salts, in particular alverine citrate, extract of butcher's broom and of horse chestnut and their combinations, a metalloproteinase inhibitor, *Schinus molle* extracts.

Under all circumstances, the person skilled in the art shall ensure that these additives as well as their proportions are selected in a way that does not adversely affect the beneficial properties sought from the composition of the invention.

In a preferred embodiment of the invention, the cosmetic, dermatological or nutracosmetic composition comprises between $10^{-6}$ and 50% by weight with respect to the total weight of the active ingredient composition.

The effective quantity of the active ingredient or plant extract corresponds to the quantity required to obtain the results sought, that is to say, improve moisturising, the barrier function of the epidermis, prevent and/or fight against the dryness of skin and mucous membranes and against the manifestations of skin ageing, aid the process of healing and depigment the skin. The anti-inflammatory activity is excluded from the claimed dermatological scope of activity.

According to an advantageous embodiment of the invention, the effective quantity or the active ingredient content in the composition of the invention is from $10^{-6}$ to 25% by weight with respect to the total weight of the composition, still more preferably from $10^{-6}$ to 10% by weight with respect to the total weight of the composition.

The indicated effective quantities are based on the results given accurately in examples 21 to 23. Thus, the effective quantity varies in the above stated proportions depending on the sucrose esters concentration of the extract and the dilution made if necessary.

According to an even more advantageous embodiment of the invention, the cosmetic composition is suitable for topical administration and mainly exists in the form of an oily, hydroalcoholic or aqueous solution or in the form of an oil-in-water or water-in-oil emulsion or multiple emulsions or in the form of creams, suspensions, or even powders; the said composition can be more or less fluid or solid and can look like a cream, lotion, milk, shampoo, serum, ointment, gel, paste, foam or a stick.

A fourth object of the invention is a cosmetic treatment process to improve the appearance of the skin, mucous membranes or skin appendages, prevent and/or fight against the dryness of skin and mucous membranes, prevent and/or fight against the cutaneous signs of ageing and/or photoageing, fight against the loss of elasticity and firmness of skin and its depigmentation, a process that includes applying an effective quantity of a cosmetic composition of the invention as defined above on the surface of the skin and/or hair.

Note that the depigmentation activity of the cosmetic composition of the invention has an inhibitory effect on the production of melanin.

A fifth object of the invention is an effective quantity of a plant extract of the invention or sucrose esters of the invention that are synthesised, alone or in combination with other active ingredients, for its or their use in the dermatological treatment of conditions that involve a pathological dryness of skin, mucous membranes or skin appendages and to promote healing.

In a preferred embodiment, the invention comprises an effective quantity of a plant extract of the invention or sucrose esters of the invention that are synthesised, alone or in combination with other active ingredients, for its or their use in the dermatological treatment of conditions that involve a pathological dryness of skin, mucous membranes or skin appendages and to promote healing, with the exception of anti-inflammatory activity.

The effective quantity is also based on the results given accurately in examples 21 to 23. The tests, mainly on collagen III, collagen IV and fibrillin-1 enable to identify an effective quantity of at least $10^{-6}$% by weight with respect to the total weight of the composition.

A sixth object of the invention is the use of an effective quantity of a plant extract of the invention or sucrose esters of the invention that are synthesised, alone or in combination with other active ingredients, to prepare a nutracosmetic composition to be ingested that is designed to improve the appearance of the skin, mucous membranes or skin appendages, prevent and/or fight against the dryness of skin and mucous membranes, prevent and/or fight against the cutaneous signs of ageing and/or photoageing.

Finally, a seventh object of the invention is a process of preparing a plant extract or active ingredient essentially comprising one or more sucrose esters.

The extraction can be carried out using a whole plant or a specific part of the plant (leaves, seeds, stems, roots, calyces, petals, fruits, etc.)

Specifically speaking, the invention uses the calyx of one of the many plants of the Solanaceae family, of the *Physalis* genus, preferably the *peruviana* species.

Any method of extraction and purification known to the person skilled in the art can be used to prepare the plant extract of the invention comprising sucrose esters as described previously and that have a biological activity on the skin, mucous membranes and skin appendages.

The preparation process of a plant extract of the invention is described in greater detail below.

The plant and its parts can be harvested by wild picking, by conventional cultivation, soilless cultivation or even hydroponic cultivation.

Non-exhaustively speaking, the process of preparing the crude extract from the plant extract can be carried out by solid/liquid plant extraction processes, which are more or less conventional, mainly using organic solvents that are well known to the person skilled in the art. The extraction process can be single-contact in batches, semi-continuous or continuous. It can also include multiple stages that are co-current or counter-current. It can be assisted by ultrasound, microwaves, thermomagnetic induction, electric fields that are pulsed or even under pressure.

The plant matrix can be prepared beforehand by drying and then grinding or freeze-grinding, flash détente [flash release] or even instant controlled pressure drop. The plant matrix can also be directed by enzymes in order to release maximum molecules of interest.

The following solvents can be used to extract the sucrose esters:
- hydrocarbons, aliphatics that are branched or linear, aromatic or cyclic like hexane, cyclohexane, etc.
- halogenated hydrocarbons, like dichloroethylene, chloroform, etc.;
- alcohols like methanol, ethanol, propanol, isopropanol or butanol, etc.
- glycols like ethylene glycol, propylene glycol, 1,2 and 1,3 propanediols, butylene glycol, glycerol, etc.
- ketones like acetone, methyl isobutyl ketone, methyl ethyl ketone, etc.
- aliphatic or cyclic ethers like diethyl ether, methyl tert-butyl ether, ethyl tert-butyl ether, Tetrahydrofuran (THF), methyl THF, etc.
- glycolethers like 2-methoxy-1-methylethyl acetate, 2-(2-butoxyethoxy) ethanol and its acetate, etc.
- esters, acids with a more or less long chain and alcohols with a more or less long chain like ethyl acetate, ethyl lactate, ethyl propionate, ethyl oleate, methyl stearate, oleyl oleate, etc.
- ionic liquids like 1-(4-sulfobutyl)-3-methylimidazolium hydrogen sulfate, 1-Ethyl-3-methylimidazolium bis (trifluoromethanesulfonyl) imide, etc.
- supercritical fluids like carbon dioxide with or without co-solvents;
- agro-solvents like vegetable oils, terpenes like limonene or pinene,
- a combination of these solvents.

The obtained extract can be purified by various methods, mainly by liquid-liquid extraction, centrifugation, adsorption (for example by decolourisation with active charcoal or bleaching clay), sublimation, crystallization, preparative chromatography, distillation mainly scraped-film or centrifugal molecular distillation or even membranous filtration.

Depending on the purification technique used, a filtration and desolvation step may be performed later if required.

In a preferred embodiment, the crude plant extract is obtained with one of the following solvents: cyclohexane, ethyl acetate and supercritical carbon dioxide with an addition of a co-solvent like an alcohol, for example an aliphatic alcohol like ethanol, or a vegetable oil, preferably refined or even an ester like caprylate/glycerol caprate.

Hence, the preparation process of a plant extract of the invention comprises Lite following steps:
- drying the part of the plant,
- grinding,
- extraction with a suitable organic solvent, followed by desolvation if required, followed by
- purification, if required, by one or more suitable methods.

In a preferred embodiment, the process of the invention comprises the following steps:
- drying the part of the plant,
- freeze-grinding,
- extraction with ethyl acetate, cyclohexane, ethanol or supercritical carbon dioxide with or without co-solvent like an alcohol or a vegetable oil or even an ester,
- purification by crystallisation or adsorption, followed by filtration if required, and
- desolvation if required.

The other advantages and characteristics of the invention will stand out better after reading the examples given by way of illustration and in a non-exhaustive manner.

EXAMPLE 1: PREPARATION OF A PLANT EXTRACT FROM THE CALYX OF *PHYSALIS PERUVIANA*

The calyces of *Physalis peruviana*, that are separated beforehand from the fruits and dried, are ground in a granulating mill, comprising a 1 mm grid, which produces a powder. The size of the particles is predominantly towards 500 μm.

The obtained powder (50 g) is placed in a cellulose thimble, which is then placed in a Soxhlet extractor.

The solvent used for the extraction is ethanol 96% (50 ml), with about twenty extraction cycles.

The extract in the solvent medium is evaporated with rotavapor to remove the solvent.

This finally leaves behind 11.0 g extract of the calyces of *Physalis peruviana* containing 57% sucrose esters.

EXAMPLE 2: PREPARATION OF A PLANT EXTRACT FROM THE CALYX OF *PHYSALIS PERUVIANA*

The calyces of *Physalis peruviana*, that are separated beforehand from the fruits and dried, are ground in a granulating mill, comprising a 1 mm grid, which produces a powder. The size of the particles is predominantly towards 500 μm.

The obtained powder (50 g) is placed in a cellulose thimble, which is then placed in a Soxhlet extractor.

The solvent used for the extraction is ethyl acetate, with about twenty extraction cycles. The extract thus obtained in the solvent medium can be purified by an on-column liquid-liquid extraction with water, at a temperature ranging between 20° C. and 65° C., counter-current in order to remove water-soluble molecules. The organic phase comprising ethyl acetate and the extract is then evaporated with rotavapor to remove the solvent.

The washed extract is drained of polyphenols, withanolides and free sugars.

This finally leaves behind 6.2 g extract of the calyces of *Physalis peruviana* containing 89.0% sucrose esters.

EXAMPLE 3: PREPARATION OF A PLANT EXTRACT FROM THE CALYX OF PHYSALIS PERUVIANA

The calyces of Physalis peruviana, that are separated beforehand from the fruits and dried, are ground in a granulating mill, comprising a 1 mm grid, which produces a powder. The size of the particles is predominantly towards 500 µm. The powder obtained (500 g) is placed in a supercritical fluid extractor.

The solvent used for the extraction is carbon dioxide with an addition of a co-solvent like an aliphatic alcohol such as ethanol.

The extraction parameters are for a pressure ranging between 75 bars and 200 bars, temperature ranging between 35° C. and 50° C., $CO_2$ flow ranging between 2 kg/h and 20 kg/h, as well as 1% to 5% ethanol with respect to $CO_2$.

The extract thus obtained in the solvent medium is decolourised with active charcoal or bleaching clay, cold crystallised and then filtered and evaporated.

This finally leaves behind 85.5 g extract of the calyces of Physalis peruviana containing 87.6% sucrose esters.

If required, the extract thus obtained can be purified by scraped-film or centrifugal molecular distillation in order to obtain an extract of the calyces of Physalis peruviana with 99.9% chromatographic purity.

EXAMPLE 4: PURIFICATION OF SUCROSE ESTERS FROM A PLANT EXTRACT OBTAINED FROM THE CALYX OF PHYSALIS PERUVIANA

An extract from the calyx of physalis (1 g) obtained in example 1 is solubilised in 6 ml of a $CH_3CN/H_2O$ solvent mixture 1:1. The solution is filtered with a thimble by Solid Phase Extraction (SPE) (C18, 10 g) which is rinsed with 10 mL of the same $CH_3CN/H_2O$ mixture 1:1.

The obtained eluate is associated with the filler solvent to obtain fraction 1 (300 mg).

The loaded thimble is then successively eluted according to the $CH_3CN/H_2O$ solvent gradient 7:3 (20 mL) and 1:0 (20 mL) to obtain 2 (500 mg) and 3 (100 mg) fractions.

Fractions 1, 2 and 3 are analysed by HPLC-DAD-DEDL and are compared to the chromatogram of the initial extract.

Fraction 1 comprises polyphenolic compounds, withanolides and physalines and polar compounds like sugars.

Fraction 2 comprises sucrose esters.

Fraction 3 is a lipid fraction.

Fraction 2 (500 mg) undergoes a fractionation by preparative HPLC (C18, 50×150 mm, 5 µm) as per a $H_2O/CH_3CN$ solvent gradient (from 3:7 to 0:1 in 35 min.) to obtain fractions:

Fraction IIIb (elution between 4 and 14 min.),
Fraction I (elution between 14 and 18 min; 230 mg),
Fraction II (elution between 18 and 25 min.; 200 mg) and
Fraction IIIa (between 25 and 35 min.).

The Fraction IIIa and IIIb fractions are brought together to obtain the Fraction III fraction (50 mg).

Composition of the obtained fractions:

Fraction I: Compound 1,3-O-(2-methyl-1-oxopropyl)-β-D-fructofuranosyl (1→2)-3,4-bis(2-methylpropanoate)-2-decanoate-α-D-glucopyranoside.

Fraction II: Compound 2,3-O-(3-methyl-1-oxobutyl)-β-D-fructofuranosyl (1→2)-3,4-bis(2-methylpropanoate)-2-decanoate-α-D-glucopyranoside.

Fraction III: sucrose esters other than previous and mainly comprising the 3-O-(3-methyl-1-oxobutyl)-β-D-fructofuranosyl(1→2)-3-(2-methylpropanoate)-2-decanoate-α-D-glucopyranoside, the 3-O-(2-methyl-1-oxopropyl)-β-D-fructofuranosyl (1→2)-3,6-bis(2-methylpropanoate)-2-decanoate-α-D-glucopyranoside.

the 3-O-(2-methyl-1-oxopropyl)-β-D-fructofuranosyl (1→2)-3-(3-methylbutanoate)-2-decanoate-α-D-glucopyranoside the 3-O-(2-methyl-1-oxopropyl)-β-D-fructofuranosyl (1→2)-3,4-bis(2-methylpropanoate)-2-nonanoate-α-D-glucopyranoside, the 3-O-(2-methyl-1-oxopropyl)β-D-fructofuranosyl(1→2)-3,4-bis(2-methylpropanoate)-2-octanoate-α-D-glucopyranoside,

EXAMPLE 5: EFFECTS OF FRACTIONS I, II AND III ON THE EXPRESSION PROFILE OF THE CUTANEOUS CELLS

The effects of fractions I, II and II have been researched on by transcriptomic analysis on models of normal human epidermal keratinocytes and human dermal fibroblasts. This global transcript expression analysis has been carried out after 4 to 24 hours of incubation by using the Affymetrix GeneAtlas™ platform and the U219 "full human transcriptome" chip containing 36,000 transcripts and variants.

1. Biological Models

Normal Human Epidermal Keratinocytes (NHEK)
  Cellular type: Normal human epidermal keratinocytes (NHEK)
  Culture conditions: 37° C., 5% $CO_2$
  Culture medium: Keratinocyte-SFM supplemented with Epidermal Growth Factor (EGF) 0.25 ng/ml Pituitary Extract (PE) 25 µg/ml Gentamycin 25 µg/ml
  Test medium: Keratinocyte-SFM supplemented with Gentamycin 25 µg/ml Normal Human Dermal Fibroblasts (NHDF)
  Cellular type: Normal human dermal fibroblasts (NHDF),
  Culture conditions: 37° C., 5% $CO_2$
  Culture medium: DMEM supplemented with
    L-glutamine 2 mM
    Penicillin 50 U/ml—Streptomycin 50 µg/ml
    Calf foetal serum (CFS) 10%
  Test medium: DMEM supplemented with
    L-glutamine 2 mM
    Penicillin 50 U/ml—Streptomycin 50 µg/ml
    CFS 1%

2. Tested Compounds

| Tested compound | Appearance/Storage | Stock solution | Tested concentration |
| --- | --- | --- | --- |
| Fraction I | Slurry Storage at +4° C. | 50 mg/ml in DMSO | 0.8 µg/ml |
| Fraction II | Slurry Storage at +4° C. | 50 mg/ml in DMSO | 0.8 µg/ml |
| Fraction III | Slurry Storage at +4° C. | 50 mg/ml in DMSO | 0.8 µg/ml |

3 Culture and Treatment

The cells have been introduced and cultivated in the culture medium for 24 hours and then incubated in their test medium for another 24 hours. Then, the medium has been replaced by the test medium containing or not containing (control) the test compounds and the cells have been incubated for 4 or 24 hours. All the conditions have been completed in n=3.

At the end of the incubation, the culture supernatants have been removed and the cell layers have been rinsed with a PBS solution. The plates have been immediately dry frozen at −80° C.

4. Principle of Use of the Affymetrix® U219 Chip—Analysis of Differential Expression Preparation of Targets The total RNA of each sample have been extracted using TriPure Isolation Reagent® as per the protocol recommended by the supplier. The quantity and quality of the RNA have been evaluated by capillary electrophoresis (Bioanalyzer 2100, Agilent).

The amplification of the RNA and the synthesis of the biotinylated RNA analogues (RNAa) have been carried out using the "GeneChip 3'IVT Express" kit (Affymetrix®). The single-strand complementary DNA (cDNA) have been synthesised by reverse transcription of the total RNA in the presence of oligo(dT). By action of a DNA polymerase, a double-stranded cDNA (ds DNA) has been synthesised. Biotinylated RNA have then been synthesised from the cDNA and in the presence of biotinylated ribonucleotide analogues. After a purification stage on magnetic beads, which enables to remove salts, enzymes and free nucleotides, the biotinylated RNA have been hydrolysed into fragments from 35 to 200 nucleotides with a peak at 100-120 nucleotides (fragmented targets).

Quality controls of the synthesised biotinylated RNA have been carried out by capillary electrophoresis (Bioanalyzer 2100, Agilent), before and after fragmentation.

Marking and Hybridisation Protocol

This step has been carried out using the "GeneAtlas™ hybridization, wash and stain kit for 3'IVT arrays" kit (Affymetrix®).

The hybridisation of the fragmented RNAa on the Affymetrix® U219 chip (36,000 transcripts and variants) has been carried out on the "GeneAtlas™ fluidics station" hybridisation station (Affymetrix®) for 20 hours at 45° C. Control probes of the hybridisation (BioB, BioC and BioD) and polyA RNA controls (Lys, Phe and Dap) have been added during hybridisation. The control probes of hybridisation, directly coupled with phycoerythrin, enable to ensure the effectiveness of the hybridisation regardless of the marking step. The poly-A RNA controls are used to validate the quality of the marking.

Then, the marking has been carried out in three steps (+ intermediate washing steps):

Fixing the streptavidin complex—phycoerythrin on the hybridised RNAa on the chip, Recognition of this complex by an anti-streptavidin antibody coupled with biotin, Addition of the streptavidin coupled with the phycoerythrin enabling an amplification of the signal.

5 Data Processing

The raw data has been transferred and processed in Microsoft Excel.

Intergroup comparisons have been made using the unpaired bilateral Student's t-test. The statistical analyses can be interpreted if n≥5; however for n<5, the calculated data is only provided for reference purposes.

Formulae used:

Standard error of the average: SE ave=standard deviation (Sd)/√n

The standard error of the average (SE aye) represents the deviation of the average of the sample with respect to the average of the actual population. The SE ave is calculated by dividing the Sd by the square root of the size of the sample.

Viability percentage: viability $(\%)=(DO_{compound}/DO_{control})\times 100$

6 Results

An analysis of "fold change" has been carried out in Excel followed by a functional analysis carried out using the Ingenuity IPA (Interactive Pathway Analysis) software. This analysis allows grouping the significantly modulated genes in biological functions (processes).

Analysis of Fibroblasts (NHDF)

The analysis of the transcriptomic profiles of the fibroblasts treated by the fractions (I, II and III) has shown an expression modulation of genes, especially with fraction II.

For fraction II, the modulation of the expression of the coding gene for fibrillin 1 (FBN1) is very interesting. In fact, the expression of this gene is significantly increased over time, 4 hours (X 3.27) and 24 hours (X 8.24).

Fibrillin 1 (major constituent of the extracellular matrix) is secreted by the fibroblasts and constitutes an important component of the microfibrils. It is mainly involved in the assembly of elastin fibres and plays an important role in the elasticity of skin.

Analysis of Keratinocytes (NHEK)

The analysis of the transcriptomic profiles of the keratinocytes treated by the 3 fractions (I, II and III) has shown an expression modulation of genes, especially with fraction III.

The treatments of keratinocytes by the 3 fractions (I, II and III) induced expression inhibitions of coding genes for differentiation proteins of the keratinocyte: KRT1, IVL, DSG1, DSC1, SPRR2A, SPRR2E, SPRR1A, SPRR2D, CALML5, SBSN and KRTDAP.

This effect enables to deduce that the I, II and III fractions have an anti differentiating effect on the keratinocytes.

In the following examples, the active ingredient of the invention can be present in different compositions in an effective quantity ranging between $10^{-6}$ to 3% by mass of the composition.

EXAMPLE 6: COMPOSITIONS TO BE ADMINISTERED ORALLY

The extract from the calyx of *Physalis peruviana*, containing sucrose esters, is integrated in oral compositions, in compositions that allow administering 50 mg to 200 mg extract per day.

1) Anti-Ageing Composition in the Form of Soft Capsule

| | |
|---|---|
| Extract from the calyx of *Physalis peruviana* as per example 1 or 2 or 3 | 30 mg |
| Argan Oil | 60 mg |
| Rich wheat germ oil in unsaponifiable matter | 300 mg |
| Vitamin of group B (B1, B2, B3, B5, B6, B9, B12) | q.s.f 100% of RDA |
| Tocotrienols | q.s.f 50% of RDA |
| Vitamin E | |
| Beeswax | |
| Soya Lecithin | |
| Edible gelatine | |
| Glycerin | q.s.f 1 soft capsule |

This composition is administered in 4 to 6 capsules per day.

2) Skin Firmness Composition in the Form of Tablets

| | |
|---|---|
| Extract from the calyx of *Physalis peruviana* as per example 1 or 2 or 3 | 25 mg |
| Cereal extracts (wheat, buckwheat, rice, quinoa) rich in sulphurised amino acids | 200 mg |
| Zinc in the form of chelate | q.s.f 100% of RDA |
| Vitamin C | q.s.f 50% of RDA |
| Glycosaminoglycans from fish cartilage | 200 mg |
| Glucidex IT 19 (compression agent) | q.s.f 1 tablet of 800 mg |

This composition is administered in 5 to 8 tablets per day.

3) Example in Chocolate-Flavoured Cereal Bar

| | |
|---|---|
| Extract from the calyx of *Physalis peruviana* as per example 1 or 2 or 3 | 200 mg |
| Lycopene | 6 mg |
| Astaxanthin | 4 mg |
| Fucoxanthin | 4 mg |
| Lutein in micro-encapsulated form | 4 mg |
| Micro-encapsulated tocotrienols | q.s.f 100% RDA in Vitamin E |
| dark chocolate, oligo-fructose, sugar, fructose syrup, fat-reduced cocoa powder, crunchy cereals, skimmed milk powder, almonds, glycerol, sorbitol, vegetable oils, glucose syrup, flavouring, sweetened condensed milk, soya lecithin, mono and diglycerides of fatty acids, caramelised syrup, maltodextrine, salt, potassium sorbate, alpha-tocopherol | q.s.f a bar of 50 g |

This composition is administered once a day.

4) Example in Vanilla-Flavoured Milk Beverage

| | |
|---|---|
| Extract from the calyx of *Physalis peruviana* as per example 1 or 2 or 3 | 200 mg |
| Extract of green tea rich in polyphenols | 100 mg |
| Vitamin of group B (B1, B2, B3, B5, B6, B9, B12) | q.s.f 100% of RDA |
| Zinc, magnesium, selenium | q.s.f 100% of RDA |
| Skimmed milk powder, flavouring, fructose, egg white, exhausted vanilla seeds, sugar, caramel, beta-carotene, xanthan gum, aspartame, potassium acesulfame, soya lecithin, maltodextrine. | q.s.f one sachet of 30 g |

This composition is administered once a day.

EXAMPLE 7: COSMETIC COMPOSITION—DAY CREAM FOR THE FACE

| INCI names | % by mass |
|---|---|
| Phase A | |
| Water | q.s.f 100 |
| Carbomer | 0.25 |
| Phase B | |
| Butylene glycol | 2.00 |
| Phenoxyethanol | qs |
| Phase C | |
| Steareth-2 | 0.40 |
| Steareth-10 | 1.20 |
| Cetearyl alcohol & Dicetyl phosphate & Ceteth 10 phosphate | 4.00 |
| Cetearyl Alcohol | 1.00 |
| Azone | 2.50 |
| Cyclohexasiloxane & Cyclopentasiloxane | 2.00 |
| Ethylhexyl succinate | 7.00 |
| Phase D | |
| Potassium sorbate | 0.10 |
| Phase E | |
| Water | 3.00 |
| Sodium hydroxide | 0.40 |
| Phase F | |
| Active ingredient of the invention (of example 1 or 2 or 3) | 2.00 |

Procedure:

Weigh phase A and let swell without stirring for 30 min. Heat phase A to 75° C. in water bath. Weigh and mix phase B. Weigh phase C and heat to 75° C. in water bath. Add phase B in phase A. Mix well. Pour phase C in phase A+B while stirring continuously. Homogenise well. Add phase D, extemporaneously. Add phase E, homogenise well. Add phase F, homogenise well.

EXAMPLE 8: COSMETIC COMPOSITION—GEL FORM FOR THE FACE

| INCI names | % by mass |
|---|---|
| Phase A | |
| Water | q.s.f 100 |
| Cetyl hydroxyethylcellulose | 0.30 |
| Phase B | |
| Carbomer | 0.40 |
| Water | 20.00 |
| Phase C | |
| Glycerin | 3.00 |
| Ethyl & Methyl & Propyl parabens | 0.30 |
| Phase D | |
| Mineral oil | 4.00 |
| Polysorbate 20 | 1.00 |
| C12-15 Alkyl Benzoate | 2.00 |
| C10-30 Alkyl Acrylate cross polymer | 0.30 |
| Phase E | |
| Potassium sorbate | 0.10 |
| Phase F | |
| Water | 5.00 |
| Sodium hydroxide | 0.50 |
| Phase G | |
| Active ingredient of the invention (of example 1 or 2 or 3) | 1.00 |

Procedure:

Disperse Phase A while stirring continuously. Sprinkle Ultrez 10 in water and let swell for 30 minutes. Heat phase C till complete dissolution. Mix Phase A with Phase B. Add C to Phase (B+A). Add Phase D while stirring continuously, to Phase (A+B+C). Add Phase E. Neutralise with Phase F. Add Phase G and mix.

EXAMPLE 9: COSMETIC COMPOSITION—SERUM FORM

| INCI names | % by mass |
| --- | --- |
| Phase A | |
| Water | q.s.f 100 |
| Carbomer | 0.25 |
| Phase B | |
| Butylene Glycol | 3.00 |
| Phenoxyethanol | 0.20 |
| Phase C | |
| Polysorbate 20 | 0.50 |
| Cetearyl Ethylhexanoate | 2.00 |
| PPG-3 Benzyl Ether Myristate | 0.50 |
| Acrylates/C 10-30 Alkyl Acrylate Cross Polymer | 0.20 |
| Cyclopentasiloxane | 1.00 |
| Phase D | |
| Potassium sorbate | 0.10 |
| Phase E | |
| Sodium hydroxide | 0.45 |
| Water | 4.00 |
| Phase F | |
| Active ingredient of the invention (example 1 or 2 or 3) | 1.00 |
| Phase G | |
| Fragrance | 0.10 |

Procedure:

Phase A: Sprinkle carbomer in water, let swell for 15 minutes. Mix Phase B. Pour Phase B into Phase A and homogenise. Then weigh Phase C, mix and add to Phase A+B while stirring continuously. Let swell for 1 hour. Extemporaneously add Phase D to the previous phase while stirring continuously. Neutralise with Phase E. Stir.

Then add Phase F. Let it mix for at least 1 hour while stirring continuously and then add Phase G. Mix well.

EXAMPLE 10: NIGHT CREAM FOR THE FACE

| INCI names | % by mass |
| --- | --- |
| Phase A | |
| Water | q.s.f 100 |
| Carbomer | 0.40 |
| Phase B | |
| Glycerin | 3.00 |
| Ethyl & Methyl & Propyl parabens | 0.30 |
| Phase C | |
| Cetearyl Alcohol & polysorbate 20 | 1.0 |
| Cetearyl Alcohol | 1.00 |
| PPG-3 Benzyl Ether Myristate | 1.0 |
| Dimethicone | 2.50 |
| Isotridecyl Isononanoate | 5.00 |
| Phase D | |
| Potassium sorbate | 0.10 |
| Phase E | |
| Sodium hydroxide | 0.40 |
| Water | 4.00 |
| Phase F | |
| Active ingredient of the invention (of example 1 or 2 or 3) | 1.00 |
| Phase G | |
| Fragrance | 0.10 |

Procedure: Weigh Phase A and let swell for 30 minutes. Heat Phase A to 75° C. in a water bath. Heat Phase B till complete solubilisation. Add Phase B to Phase A. Heat Phase C to 75° C. in a water bath. Add Phase C to Phase A+B while stirring continuously. Add Phase D and homogenise well. Neutralise with Phase E at 55° C. Add Phase F then Phase G and homogenise well.

EXAMPLE 11: BODY CREAM

| INCI names | % by mass |
| --- | --- |
| Phase A | |
| Water | q.s.f 100 |
| Carbomer | 0.4 |
| Phase B | |
| Glycerin | 3.00 |
| Ethyl & Methyl & Propyl parabens | 0.30 |
| Phase C | |
| Sorbitan stearate | 2.00 |
| Mineral Oil | 4.00 |
| PPG-3 Benzyl Ether Adipate | 1.00 |
| Glyceryl stearate & PEG 100 stearate | 3.00 |
| Phase D | |
| Potassium sorbate | 0.10 |
| Phase E | |
| Sodium hydroxide | 0.40 |
| Water | 4.00 |
| Phase F | |
| Active ingredient of the invention (of example 1 or 2 or 3) | 2.00 |
| Phase G | |
| Fragrance | 0.10 |

Procedure: Weigh Phase A and let swell for 30 minutes. Heat Phase A to 75° C. in a water bath. Heat Phase B till complete solubilisation. Add Phase B to Phase A. Heat Phase C to 75° C. in a water bath. Add Phase C to Phase A+B while stirring continuously. Add Phase D and homogenise well. Neutralise with Phase E at 55° C. Add Phase F then Phase G and homogenise well.

EXAMPLE 12: LOTION

| INCI names | % by mass |
| --- | --- |
| Phase A | |
| Water | q.s.f 100 |
| Phase B | |
| Butylene Glycol | 5.00 |
| Phenoxyethanol | 0.20 |

-continued

| INCI names | % by mass |
|---|---|
| Phase C | |
| Polysorbate 20 | 2.00 |
| PPG-3 Benzyl Ether Myristate | 0.10 |
| Phase D | |
| Potassium sorbate | 0.10 |
| Phase E | |
| Active ingredient of the invention (of example 1 or 2 or 3) | 1.00 |
| Phase F | |
| Fragrance | 0.10 |

Procedure: Weigh Phase A. Weigh Phase B and mix. Add Phase B to Phase A while stirring continuously for 30 minutes. Weigh Phase C, mix till the mixture is homogeneous. Add Phase C to Phase A+B while stirring continuously. Add Phase D to the previous mixture. Add Phase E to the previous mixture while stirring continuously. Homogenise well. Weigh Phase F, mix and add to the previous mixture. Mix continuously.

EXAMPLE 13: DAY CREAM

| INCI names | % by mass |
|---|---|
| Phase A | |
| Water | q.s.f 100 |
| Carbomer | 0.2 |
| Phase B | |
| Butylene Glycol | 2.00 |
| Phenoxyethanol | 1.30 |
| Phase C | |
| Glyceryl stearate & PEG 100 stearate | 1.00 |
| Caprylic/capric Triglycerides | 4.00 |
| Phase D | |
| Acrylates/C10-30 Alkyl Acrylates cross polymer | 0.20 |
| PPG-3 Benzyl Ether Myristate | 1.00 |
| Dimethicone | 1.00 |
| Phase E | |
| Sorbate | 0.10 |
| Phase F | |
| Sodium hydroxide | 0.40 |
| Water | 4.00 |
| Phase G | |
| Active ingredient of the invention (of example 1 or 2 or 3) | 2.00 |
| Phase H | |
| Fragrance | 0.10 |

Procedure: Phase A: Pour Ultrez 10 in water and let swell for 30 minutes. Weigh Phase B and let melt at 60° C. Heat Phase A to 75° C. in a water bath. Weigh Phase C and heat to 75° C. in a water bath. While stirring continuously (Staro s=500 rpm), add Phase C to Phase A. Randomly, add Phase B and Phase D to Phase A+B and then add Phase E to it. Homogenise well. Cool to 45° C. and add Phase F. Add Phase G at 35° C. and homogenise well. Add Phase H and homogenise well.

EXAMPLE 14: FLUID FOR THE BODY

| INCI names | % by mass |
|---|---|
| Phase A | |
| Water | 5.00 |
| Carbomer | 0.30 |
| Phase B | |
| Water | q.s.f 100 |
| Hydroxyethyl cellulose | 0.40 |
| Phase C | |
| Butylene Glycol | 3.00 |
| Phenoxyethanol | 1.30 |
| Phase D | |
| C12-C15 Alkyl Benzoate | 2.00 |
| Caprylic/capric Triglyceride | 3.00 |
| Polysorbate 20 | 1.00 |
| PPG-3 Benzyl Ether Myristate | 1.00 |
| Acrylates/C10-30 Alkyl Acrylates cross polymer | 0.20 |
| Phase E | |
| Sorbate | 0.10 |
| Phase F | |
| Sodium hydroxide | 0.50 |
| Water | 5.00 |
| Phase G | |
| Active ingredient of the invention (of example 1 or 2 or 3) | 2.00 |
| Phase H | |
| Fragrance | 0.10 |

Procedure: Phase A: Pour Ultrez 10 in water and let swell for 30 minutes. While stirring with a propeller mixer (300 rpm), pour Phase B and let swell for 1 hour. Add Phase A to Phase B while stirring with a propeller mixer (300 rpm), and homogenise well. Weigh and stir Phase C, weigh Phase D and mix. Add Phase C to Phase A+B. Add Phase D to Phase A+B+C. Homogenise well. Add Phase E then Phase F and G and finally Phase H. pH=6.2.

EXAMPLE 15: NIGHT CREAM

| INCI names | % by mass |
|---|---|
| Phase A | |
| Water | 5.00 |
| Carbomer | 0.30 |
| Phase B | |
| Water | q.s.f 100 |
| Hydroxyethyl cellulose | 0.40 |
| Phase C | |
| Butylene Glycol | 3.00 |
| Phenoxyethanol | 1.30 |
| Phase D | |
| PPG-3 Benzyl Ether Myristate | 1.00 |
| Acrylates/C10-30 Alkyl Acrylates cross polymer | 0.20 |
| Phase E | |
| Sorbate | 0.10 |
| Phase F | |
| Sodium hydroxide | 0.50 |
| Water | 5.00 |

-continued

| INCI names | % by mass |
|---|---|
| Phase G | |
| Active ingredient of the invention (of example 1 or 2 or 3) | 2.00 |
| Phase H | |
| Fragrance | 0.10 |

Procedure: Phase A: Pour Ultrez 10 in water and let swell for 30 minutes. While stirring with a propeller mixer (300 rpm), pour Phase B and let swell for 1 hour. Add Phase A to Phase B while stirring with a propeller mixer (300 rpm), and homogenise well. Weigh and stir Phase C, weigh Phase D and mix. Add Phase C to Phase A+B while stirring with a blade mixer (300 rpm). Add Phase D to Phase A+B+C. Homogenise well. Add Phase E then Phase F and G and finally Phase H. Homogenise well.

EXAMPLE 16: ANTI-STRETCH MARKS CREAM

| INCI names | % by mass |
|---|---|
| Phase A | |
| Water | q.s.f 100 |
| Carbomer | 0.40 |
| Phase B | |
| Glycerin | 5.00 |
| Phenoxyethanol (and) Mixed Parabens | 0.80 |
| Phase C | |
| Ethylhexyl Palmitate | 4.00 |
| Cetearyl alcohol Croda | 0.50 |
| Myristyl Lactate | 0.30 |
| Polysorbate 20 | 1.00 |
| Phase D | |
| Acrylates/C10-30 Alkyl Acrylates cross polymer | 0.20 |
| Cyclomethicone | 2.00 |
| Phase E | |
| Potassium sorbate | 0.10 |
| Phase F | |
| Sodium hydroxide | 0.60 |
| Water | 6.00 |
| Phase G | |
| Active ingredient of the invention (of example 1 or 2 or 3) | 1.00 |
| Phase H | |
| Fragrance | 0.10 |

Procedure:

Phase A: Disperse Ultrez 10 in water and let swell for 20 minutes. Mix Phase B and heat to 60° C. till complete dilution. Add Phase B to Phase A while stirring continuously. Heat Phase A+B. Weigh Phase C and heat to 75° C. Add Phase C to Phase A+B while stirring continuously. Homogenise carefully and then add Phase D. Add Phase E. Neutralise with Phase F at 50° C. Add Phase G and H at 35° C. and adjust the pH at 6.3 with NaOH.

EXAMPLE 17: HAIR LOTION

| INCI names | % by mass |
|---|---|
| Phase A | |
| Cetrimonium Chloride | 1.00 |
| Citric acid | 0.22 |
| Trisodium Citrate | 1.20 |
| Sorbate | 0.10 |
| Water | q.s.f 100 |
| Phase B | |
| Methyl Paraben | 0.20 |
| PPG 5 Ceteth 20 | 2.00 |
| Phase C | |
| Active ingredient of the invention (of example 1 or 2 or 3) | 1.00 |
| Phase D | |
| Polysorbate 20 | 1.00 |
| Fragrance | 0.10 |

EXAMPLE 18: MOISTURISING MAKE-UP

| INCI names | % by mass |
|---|---|
| Phase A | |
| Water | q.s.f 100 |
| Caustic potash | 1.3 |
| Polysorbate 80 | 0.1 |
| Phase B | |
| Titanium dioxide | 6.00 |
| Talc | 3.05 |
| Yellow iron oxide | 1.8 |
| Red iron oxide | 1.00 |
| Black iron oxide | 0.15 |
| Phase C | |
| Propylene glycol | 4.00 |
| Magnesium Aluminium Silicate | 1.00 |
| Phase D | |
| Propylene glycol | 2.00 |
| Sodium Carboxymethylcellulose | 0.12 |
| Phase E | |
| Di-PPG-3 Myristyl Ether Adipate | 12.00 |
| Isostearyl Neopentanoate | 4.00 |
| Cetearyl Alcohol, Ceteth-20 Phosphahte, Dicetyl Phosphate | 3.00 |
| Steareth-10 | 2.00 |
| Cetyl alcohol | 0.62 |
| Steareth-2 | 0.5 |
| Phase F | |
| Active ingredient of the invention (of example 1 or 2 or 3) | 3.00 |

EXAMPLE 19: LIP BALM

| INCI names | % by mass |
|---|---|
| Phase A | |
| Water | q.s.f 100 |
| Potassium sorbate | 0.10 |
| Magnesium sulphate | 0.70 |

-continued

| INCI names | % by mass |
|---|---|
| Phase B | |
| Cetyl Dimethicone Copolyol | 3.00 |
| Methyl Paraben | 1.00 |
| Tribehenin | 0.30 |
| PPG-3 BEnzyl Ether Myristate | 2.00 |
| *Argania spinoa* Kernel Oil | 19.00 |
| Phase C | |
| Active ingredient of the invention (of example 1 or 2 or 3) | 0.50 |
| Phase D | |
| Fragrance | 0.10 |

Procedure: Heat Phase A to 85° C. Mix Phase B and heat to 85° C. Slowly add Phase A to Phase B while stirring continuously (Staro s=3000 rpm then 1200 rpm). Add Phase C preheated to 80° C., and homogenise. Add Phase D at 35° C. Pour.

EXAMPLE 20: HAIR PROTECTING SPRAY

| INCI names | % by mass |
|---|---|
| Phase A | |
| Water | q.s.f 100 |
| Ethanol | 10.00 |
| Polysorbate 20 | 0.40 |
| Cetrimonium Chloride | 1.00 |
| Phase B | |
| Butylene glycol (and) *Helianthus Annus* Seed Extract | 5.00 |
| Preservative | Qs |
| Phase C | |
| Active ingredient of the invention (of example 1 or 2 or 3) | 3.00 |
| Phase D | |
| Water | 0.50 |
| Sodium hydroxide | 0.05 |

Procedure: Weigh and mix Phase A with a blade stirrer s=300 rpm. Add Phase B, mix and then add Phase C. Adjust the pH between 5.0 and 5.5 with Phase D.

EXAMPLE 21: TESTS DEMONSTRATING THE ANTI-AGEING AND REJUVENATING ACTIVITY OF THE UCHUVA EXTRACT

In the figures accompanying examples 21 to 23, the Uchuva extract is shortened to EUc. In all these examples 21 to 23, the Uchuva extract comes from the extraction process described in example 3 presenting 99.9% chromatographic purity in sucrose esters.

The dermis provides a solid support to the epidermis and is also its nourishing element. It mainly comprises fibroblasts and an extracellular matrix mainly comprising collagens, elastin and a substance called basic substance. These components are synthesised by fibroblasts. The dermo-epidermal junction ensures the cohesion between the epidermis and the dermis.

The collagens are predominantly proteins of the extracellular matrices of the skin. Twenty types of collagens are identified and noted from I to XX till date. The collagens that are predominantly present in the entire dermis are collagens of type I and III that form the extracellular matrix of the entire dermis (these are these collagens that constitute 70%-80% of the dry weight of the dermis). The dermis becomes thinner with age and wrinkles appear on the surface of the skin. As a result, in view of the important role that collagen plays in the integrity of the skin and its resistance to external mechanical aggressions, the stimulation of the synthesis of these collagens, and especially collagen of type I and III, seems to be an effective way to offset the signs of skin ageing (review by Tzaphlidou M., *Micron* 35 (2004) 173-177).

Collagen I and III Targets

Collagen I is the chief Collagen that gives the skin its mechanical resistance.

This protein represents 90% of the collagen of a vertebrate. It constitutes the bone framework (to be compared with reinforced concrete reinforcements), and more generally the common connective tissues. It is found in bones, skin, tendons, cornea and the internal organs.

1—Study on Young Cells Versus Old Cells

The following study enabled studying the effect of the Uchuva extract on the expression of collagen I, an essential constituent of the extracellular matrix of the dermis.

Method

The NHDF (Normal Human Dermal Fibroblasts) young or aged by replicative senescence have been introduced in 96 wells plate and incubated for 24 hours at 37° C., 5% CO2.

The cells have been treated for 24 hours in the presence of test products.

Then, the cells have been fixed with formalin and the expression of the proteins has been detected by immunofluorescence.

The fluorescent markings have been imaged and quantified by automated microscopy (Arrayscan Cellomics™). The fluorescence has been quantified by the Compartimental Analysis bioapplication.

Prior Evaluation of Cytotoxicity

The compound has been kept in contact with the cells for 24 hours. During the last three hours of the colorimetric test, ready-to-use WST1 of Roche® has been introduced in the medium.

This reagent contains tetrazolium salts, a violet indicator. This reagent is cleaved to formazan, a yellow indicator, by cellules metabolically active cells. Thus, the level of yellow colouring is proportional to the number of living cells. The measurement of the absorbance is done at 450 nm. The test considers that a value lower than 90% of the control element indicates a possible cytotoxicity of the product (symbolised by a green line on the graphs). This can also indicate that the metabolic activity of the cells has been reduced. A value lower than 75% indicates significant cytotoxicity (symbolised by a red line on the graphs).

In addition, the cells have been observed under the microscope to observe and compare their physiognomy.

The results are given in FIG. 1A.

The Uchuva extract is cytotoxic with stronger tested concentrations from 100 to 20 ppm and becomes less cytotoxic from 2 ppm.

Concentrations Retained to be Tested:

The Uchuva Extract is tested with the following concentrations 2-1-0.5 ppm.

Figure 1B:
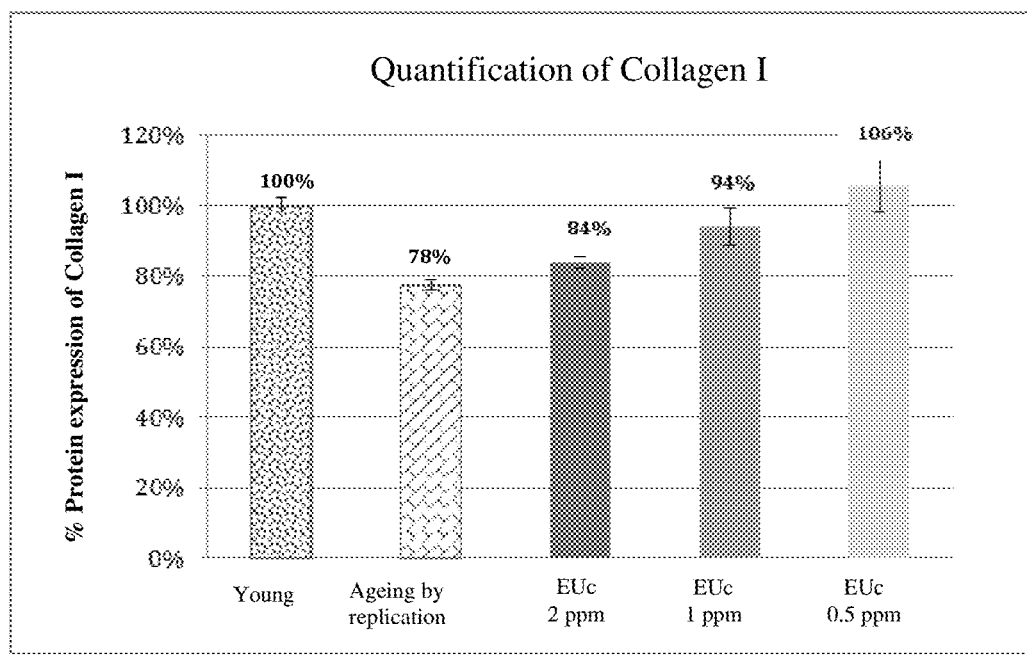

The results are given in FIG. 1B.

The Uchuva extract allows re-establishing the Collagen I expression at the level of young cells.

In young cells, the expression of Collagen I is not homogeneous. Some cells show a high marking while others have a lower marking. In cells aged by replication, the expression reactivated by the Uchuva extract is more homogeneous in the treated cells.

The fact that the lowest concentration is active can be explained by the fact that the highest concentrations show a slight cytotoxicity that affects the protein synthesis.

Conclusion

The Uchuva extract is an ingredient that acts on collagen I, the target of skin ageing, by re-establishing the protein expression up to the expression observed in young cells.

2—Evaluation of the Effect of the Uchuva Extract on Collagen I Production by Fibroblasts Materials and Methods Used Test System Description: Human Fibroblasts Model (NHDF) in culture used between passages 3 to 6.

Culture medium: DMEM glucose 4.5 g/L+1% NEAA+ 10% SVF

Culture conditions: 37° C., 5% CO2

Culture Method and Treatment of Fibroblasts

Evaluation of the Cytotoxicity by the Test of Neutral Red

The NHDF cells are introduced on D0, in 96 wells plaque, at a rate of $4 \times 10^3$ cells per well. They are treated on D1 for 48 hours with culture in a complete medium.

The concentrations of the active to be tested are expressed in % of the extract. The stock solution of the product to be tested has been prepared in dimethyl sulfoxide (DMSO) with 20% concentration (w/v). The first dilution has been made to 1/1000th. The following dilutions have been made to ½ while maintaining the final DMSO concentration at 0.1%.

The NR test is carried out on D3: the medium is removed and the cells are rinsed with 250 µL of PBS preheated to 37° C. 200 µl of neutral red are added to the cells. After 3 hours of incubation at 37° C., 5% CO2, the medium containing the neutral red is removed and then the cells are rinsed with 2×200 µl of PBS preheated to 37° C. 100 µl of the revelation solution (50% ethanol—1% acetic acid) are added and the cells are incubated at ambient temperature while stirring continuously and sheltered from light for 45 minutes.

The DO540 nm is measured after homogenisation.

NB: Preparation of the neutral red solution: the neutral red stock solution is prepared at 0.4% in Ultra Pure water (this solution is preserved at 4° C. for 15 days). It is diluted extemporaneously to 1/80th in the complete culture medium and then centrifuged for 10 minutes at 3000 revolutions per minute (rpm) before use.

Evaluation of the Metabolic Activity by the MTT (Methyl Thiazol Tetrazolium) Test The NHDF cells are introduced on D0, in 96 wells plaque, at a rate of $4 \times 10^3$ cells per well. They are treated on D1 for 48 hours with culture in a complete medium.

The concentrations of the active to be tested are expressed in % of the extract. The stock solution of the extract has been prepared in DMSO with 20% concentration (w/v). The first dilution has been made to 1/1000th. The following dilutions have been made to ½ while maintaining the final DMSO concentration at 0.1%.

The MTT test is carried out on D3: the medium is replaced by 100 µL of MTT at 0.5 g/L in a complete medium. After 3 hours of incubation at 37° C., 5% CO2, the MTT solution is replaced by 100 µL of DMSO. The DO540 nm is measured after homogenisation (amount condition as stated for the previous test with neutral red).

Preparation Method and Tested Product

Description of the product to be tested: Uchuva Extract

After the first two tests given above, three concentrations of the product to be tested have been selected for the rest of the tests to be carried out: $8.10^{-5}$%(0.8 ppm), $16.10^{-5}$% (1.6 ppm) and $32.10^{-5}$% (3.2 ppm)

Dose of Collagen I in the Culture Supernatants by ELISA Method

The cells are introduced on D0, in 6 wells plates, at a rate of $25 \times 10^3$ cells per well. They are treated on D1 for 48 hours with culture in a complete medium.

The concentrations of the active to be tested are expressed in % of the extract. The stock solution of the extract has been prepared in DMSO with 20% concentration (w/v). The first dilution has been made to 1/1000th. The following dilutions have been made while maintaining the final DMSO concentration at 0.016% (corresponding to the DMSO concentration in the strongest concentration of the extract).

After 48 hours, the culture supernatants are recovered and stored at −80° C.

The collagen I dose is administered as per the instructions of the supplier of the ELISA kit (Tecomedical).

Effect of the Uchuva Extract on Collagen I Production by Fibroblasts in 48 Hours Culture:

Table Presenting the Quantities of Collagen I (ng) for 104 Cells:

| Conditions $2.5 \times 10^4$ cells/well dilution to 1/5 | No. of cells by condition (×$10^4$) | Col I quantity in ng/$10^4$ D01 cell | Col I quantity in ng/$10^4$ D02 cell | Col I quantity in ng/$10^4$ D03 cell | Col I quantity in ng/$10^4$ D04 cell | Average | Standard deviation |
|---|---|---|---|---|---|---|---|
| Control element | 14 | 49.4 | 48.1 | 49.7 | 49.0 | 49.0 | 0.71 |
| DMO [bone mineral density] control element | 16 | 47.5 | 48.9 | 46.0 | 50.5 | 48.2 | 1.93 |
| Uchuva Extract (EUc) $8 \times 10^{-5}$% | 12 | 57.6 | 69.8 | 64.8 | 59.5 | 63.0 | 5.5 |
| Uchuva Extract (EUc) $16 \times 10^{-5}$% | 12 | 63.8 | 63.8 | 65.5 | 63.0 | 64.0 | 1.06 |
| Uchuva Extract (EUc) $32 \times 10^{-5}$% | 13 | 52.7 | 56.1 | 47.3 | 50.2 | 51.6 | 3.74 |

These results enable to observe a significant increase in the production of Collagen I by 29% and 30% by the fibroblasts treated for 48 hours by the Uchuva extract with lower concentrations ($8.10^{-5}$% and $16.10^{-5}$% respectively) with respect to the control element.

With the highest concentration ($32.10^{-5}$%), the production of Collagen I by the fibroblasts reduces to a level close to the controlled conditions. This decrease can be explained by a starting of cellular toxicity at this high level of concentration.

Figure 2A:
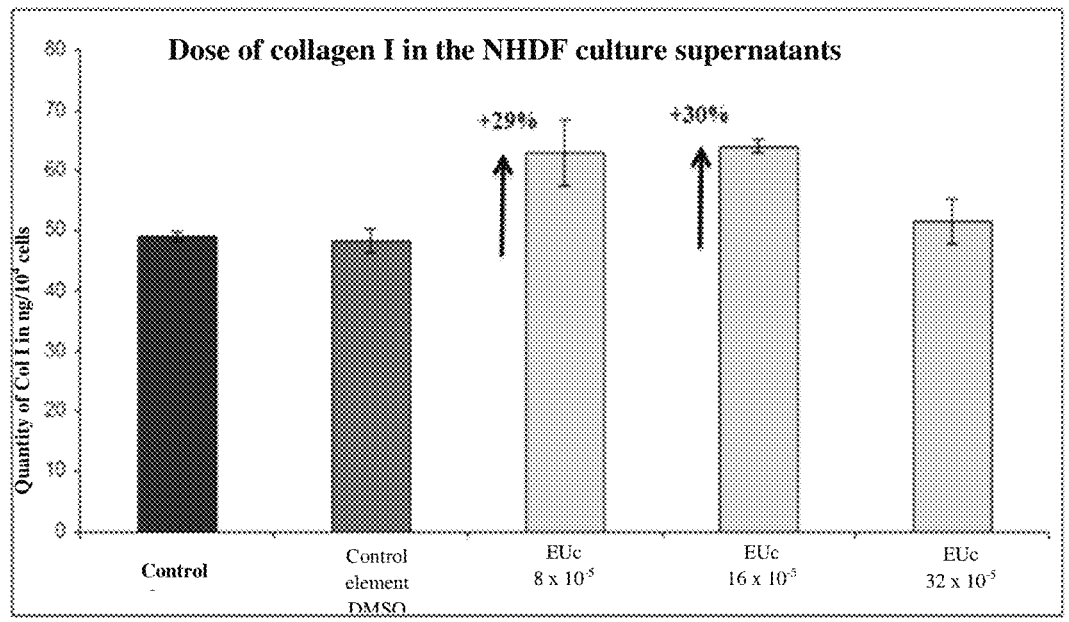

The results are in FIG. 2A.

3—Evaluation of the Effect of the Uchuva Extract on the Production of Collagen III by the Fibroblasts The cells are introduced on D0, in 6 wells plates, at a rate of $25 \times 10^3$ cells per well. They are treated on D1 for 48 hours with culture in a complete medium.

The concentrations of the active to be tested are expressed in % of the extract. The stock solution of the extract has been prepared in DMSO with 20% concentration (w/v). The first dilution has been made to 1/1000th. The following dilutions have been made while maintaining the final DMSO concentration at 0.016% (corresponding to the DMSO concentration in the strongest concentration of the extract).

| EUc | EUc | EUc |
|---|---|---|
| 8 × 10−5% | 16 × 10−5% | 32 × 10−5% |

After 48 hours, the culture supernatants are recovered and stored at −80° C.

The collagen III dose is administered as per the instructions of the supplier of the ELISA kit (SunRed).

Effect of the Uchuva Extract on Collagen III Production by Fibroblasts in 48 hours Culture:

Table below presenting the quantities of collagen III (μg) for 104 cells:

| Quantity of Collagen III in μg/$10^4$ cells | AVERAGE | AND |
|---|---|---|
| Control element | 0.78 | 0.21 |
| DMO [bone mineral density] control element | 0.82 | 0.17 |
| Uchuva Extract (EUc) 8 × $10^{-5}$% | 0.9 | 0.34 |
| Uchuva Extract (EUc) 16 × $10^{-5}$% | 1.17 | 0.11 |
| Uchuva Extract (EUc) 32 × $10^{-5}$% | 0.86 | 0.06 |

The analysis of these results highlights an increase of the concentration dependent on the production of Collagen III induced by the Uchuva extract. The production is maximum at the concentration of 16.10-5% (+50% with respect to the control elements).

At the highest concentration of the extract (32.10-5%), the production of Collagen III by the fibroblasts reduces to a level close to that of the control condition as in the case of the production of Collagen I. This observation confirms the presence of a cellular toxicity at this level of concentration.

Figure 2B:
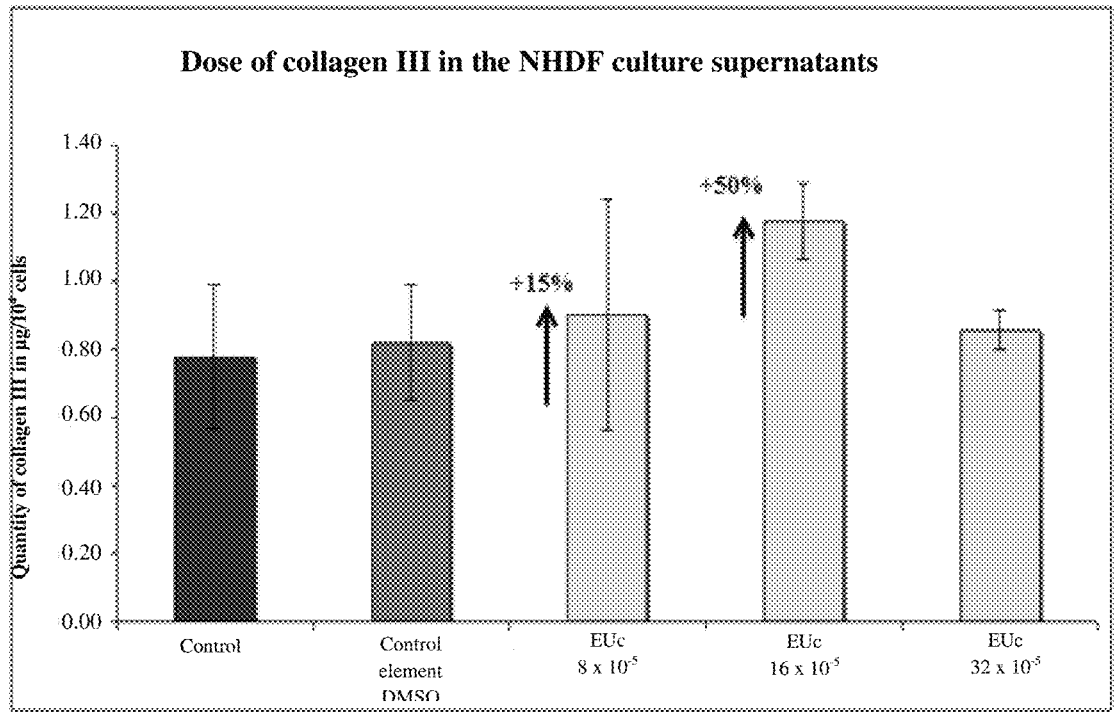

The results are in FIG. 2B.

4—Evaluation of the Effect of the Uchuva Extract on the Collagen IV Target

Collagen is the major constituent of the MEC (approx. 70%) synthesised by fibroblasts. There are fibrillar (I, II, III, V, XI) and non-fibrillar (IX, XII, XIV, XVI) collagens. Collagen fibres are flexible and they resist tension forces in the tissues. They form undulating beams with variable thickness and length. Collagen of type IV is special. It forms the "primary network" of the basal membranes (lamina densa). It is involved in cellular adhesion, proliferation, migration and angiogenesis (melanoma). It has a site of interaction with the integrin receptor. It is at the point of contact between the basal plate and the MEC (S Pasco et al., *Cancer Detection and Prevention*, 29, 260, 2005). Collagen IV, with laminins 1, forms a network that constitutes the structure of the basal membrane for a structural and functional maintenance of the tissues.

The two concentrations of 4.10-5% and 8.10-5% of the Uchuva extract have been tested.

Evaluation of the Quantity of Proteins of the Extracellular Matrix Produced by Fibroblasts During 48 Hours Detection of the Expression of Collagen IV by Immunocytology The cells are introduced on D0, in Millicell 8 wells slides, at a rate of 4.103 cells per ml in 400 μl of complete medium. They are treated on D1 for 48 hours with culture in a complete medium. The concentrations of the active to be tested are expressed in % of the extract. The stock solution of the extract has been prepared in DMSO with 20% concentration (w/v). The first dilution has been made to 1/1000th. The following dilutions have been made while maintaining the final DMSO concentration at 0.1%. After 48 hours, the cells are fixed by an alcohol/acid mixture. Then, the cells are marked using an anti-collagen IV antibody (Rockland) diluted in PBS+BSA/tween to 1/50 for 1 hour. The slides are then rinsed twice by PBS. The revelation of the specific marking is done using an FITC coupled secondary antibody (Santa-Cruz) diluted in PBS+BSA/tween to 1/100 for 1 hour. The slides are then rinsed twice by PBS and put between the slide and the cover glass using the Roti-Mount Fluocare+DAPI (Roth) mounting fluid.

Photos in green and blue are taken using a DP72 camera (Olympus, Japan) connected to a BX-60 epifluorescence microscope (Olympus, Japan).

The photos have been observed by two readers and a scoring of the intensity of fluorescence has done on a linear scale from 0 (no marking) to 4 (very high marking).

Figure 3A:
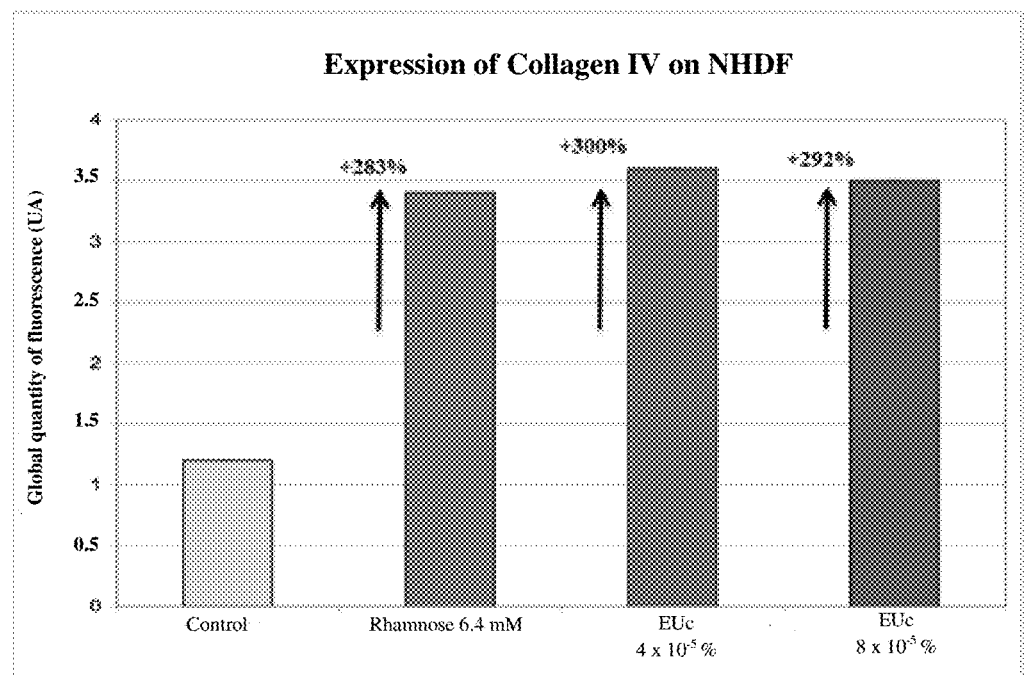

At the same time, a concentration of rhamnose has been integrated in this test as a positive control element for the expression of Collagen IV. In fact, rhamnose and polysaccharides containing rhamnose are described to induce the synthesis of collagens in fibroblasts[22]. The results are in FIG. 3A.

The analysis of the results shows a great increase of the expression of Collagen IV (approx. +300%) in fibroblasts treated for 48 hours by the UCHUVA extract, irrespective of the concentration used. The amplitude of this increase in expression of Collagen IV is comparable to that obtained with rhamnose.

5—Evaluation of the Effect of the Uchuva Extract on the Elastin Target

Elastin is a structural glycoprotein (like laminin and fibronectin) used in the composition of the MEC. It is a protein of the family of structural fibrous proteins. It is secreted by fibroblasts essentially during the period of growth, and has elastic properties. Its synthesis reduces with age and elastin is replaced by inextensible collagen. Striae atrophicae is a visible example of this process, which is related to mechanical constraints. Its second example is skin ageing.

In the Extracellular Matrix:

The elastin is synthesised and secreted in the extracellular space by the fibroblasts first as proelastin, then as tropoelastin. It is the major component (up to 90%) of the elastic fibres plus fibrillin Hence, collagen associated with elastin and fibrillin that form the elastic fibres, by covalent cross-linked bonds, are the main constituents of the extracellular matrix. The total production of elastin stops around puberty. After this, the quantity of the available elastin will reduce with time.

Degradation:

The degradation of elastin is related to the action of elastase, anenzyme that is secreted by the fibroblasts. The enzymatic action of elastase is inhibited by al-antitrypsine. The inhibition of the degradation creates a balance increasing the stability of elastin.

Role:

There are distinctive traits that characterise elastin: it enables cells to bind and enable the biological tissues to be formed. Thus, the proper functioning of the skin, lungs, blood vessels, connective tissues, certain tendons and cartilage is closely related to the characteristics of elastin. Like its name suggests, elastin is elastic. With an equal diameter, it is five times more elastic than a rubber band. It can stretch up to 150% of its normal length before breaking. Thus, it enables the tissues to stretch and be restored to their initial status after the stretching, which makes them supple.

The Dermis:

Elastin is present in the dermis of the skin and acts as a support. For example, during ageing, the loss of elasticity and tonicity of the dermis that can no longer fight the effects of the contraction of subjacent muscles leads to the appearance of wrinkles. In addition, the exposure to ultraviolet radiation increases the degradation of elastin.

Study on Young Cells Versus Aged Cells

The following study enabled studying the effect of the Uchuva extract on the expression of the elastin protein.

Method

The NHDF (Normal Human Dermal Fibroblasts) young or aged by replicative senescence have been introduced in 96 wells plate and incubated for 24 hours at 37° C., 5% CO2.

The cells have been treated for 24 hours in the presence of test products. Then, the cells have been fixed with formalin and the expression of the proteins has been detected by immunofluorescence. The fluorescent markings have been imaged and quantified by automated microscopy (Arrayscan Cellomics™). The fluorescence has been quantified by the Compartimental Analysis bioapplication.

Cellular Models:

Young: NHDF of young donor (25 years)

Ageing by replicative senescence: NHDF of young donor cultivated over several times till the stage of senescence.

Figure 3B:
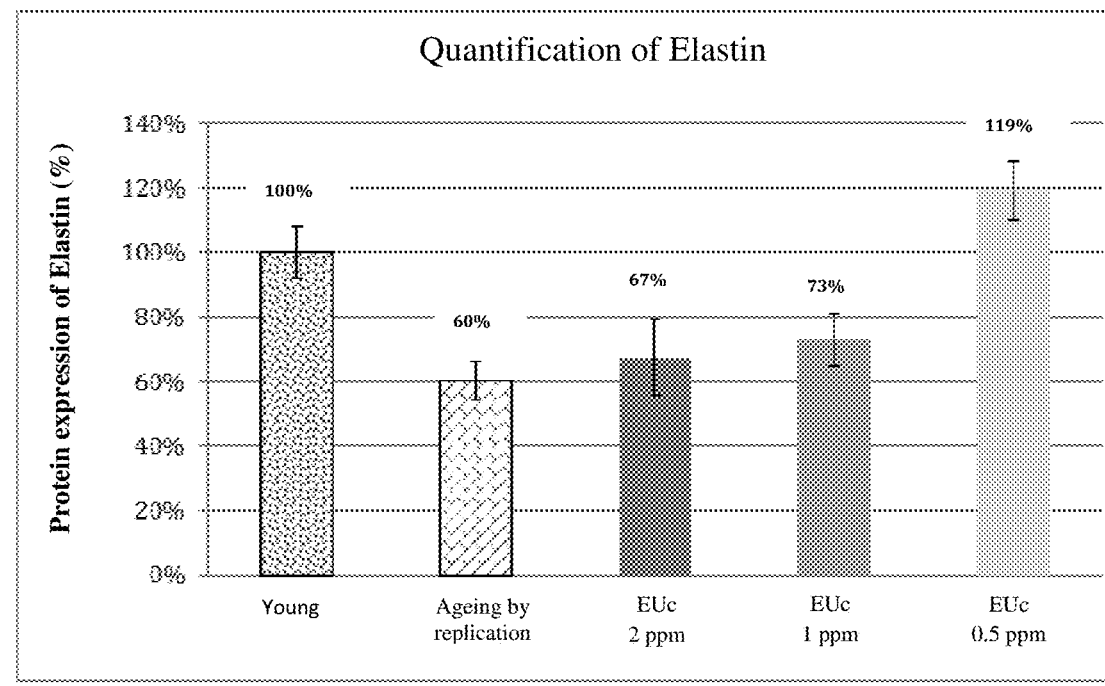

The results are in FIG. 3B.

The Uchuva extract allows re-establishing the Elastin expression slightly above the protein level of young cells.

Conclusion

In view of the results obtained, the Uchuva extract shows an improvement of the elasticity in vitro that can be extrapolated in vivo.

6—Evaluation of the Effect of the Uchuva Extract on the Methylation Target of the DNA The methylation is a modification of the N-terminal ends of the histones. It can be carried out either on lysines or on arginines and can materialise by the addition of one, two or three methyl groups. Depending on the methylated residues and the number of added groups it is associated to activation or repression of the transcription. Considered to be static for a long time, the methylation of histones proves to be a reversible modification involved in a dynamic process, though it is more stable than acetylation and phosphorylation. An increasing number of demethylase histones are identified. Generally, this type of modifications opposes acetylation, and the deacetylation of lysines should take place before their methylation. This opposition leads to the establishment of a certain dynamic balance between the heterochromatin (generally non expressible and methylated on certain key amino acids) and euchromatin territories (generally expressible and acetylated). For example, Lysine 9 of histone H3 is known to be associated with a repression of the surrounding chromatin when it is methylated. This methylation is recognised by a protein, HP1, which thus fixes on methylated H3. HP1 attracts the Suv39 protein, a Histone MethylTransferase, which can methylate lysine 9 of histone H3 of the neighbouring nucleosome, and so on. We can thus see, step by step, how histones H3 will be methylated and the chromatin, condensed. However, this heterochromatin invasion will be stopped if the encountered lysine 9 of H3 is already acetylated. Hence, a competitive balance is established between expressed and repressed chromatin domains. The modifications of the histone tails play the role of epigenetic "marks" that lead to the recruitment of different protein classes, as the acetylated or methylated lysines are recognised by different protein domains. Moreover, the recruitment of certain factors at the level of the chromatin requires the prior existence of modifications of histones and proteins that are already linked. The code of the histones is thus interpreted in the context of other factors associated to the chromatin, and it is the interaction combination between the modified histones and other factors that determines whether a protein is recruited to the chromatin. Ageing affects all the tissues of organisms. This process is related to the epigenetic modifications like changes of methylation at the level of specific cytosine residues of the DNA, as described in several publications[24-31]. The role of the epigenetic modifications in ageing, accumulation of cell divisions and deteriorated macromolecules contribute to an aged phenotype. The unpredictable and environmental events can also modify this phenotype through epigenetic mechanisms like methylation of the DNA and the methylation and acetylation of histones. The potential reversibility of the epigenetic modifications makes them attractive targets for the treatment of conditions related to ageing.

Study on Young Cells Versus Aged Cells

In order to understand the reactivation mechanism of the expression of the proteins observed, we carried out an analysis of the methylation of the DNA on aged cells in an intrinsic manner. In fact, one of the characteristic features of cellular senescence is the accumulation of methylated zones in the DNA, at the level of the Cytosines contained in the CpG dinucleotides. This leads to the deactivation of promoters and decrease in the expression of certain genes.

Method

The NHDF (Normal Human Dermal Fibroblasts) young or aged intrinsically by replication have been introduced in 6 wells plate and incubated at 37° C., 5% CO2 till subconfluence. The cells have been treated for 24 hours in the presence of test products. Then, the cells have been taken off in the presence of trypsin, and lysed. The genomic DNA has been precipitated with Ethanol. The methylation rate of the DNA has been measured by ELISA using the Enzo kit: 5-Methylcytosine DNA ELISA kit. The values are represented from 50% for better visibility of the results.

Cellular Models:

Young: NHDF of young donor (25 years)

Ageing by replicative senescence: NHDF of young donor cultivated over several times till the stage of senescence.

Following the prior evaluation of its cytotoxicity, the Uchuva Extract is tested with the following concentrations 2-1-0.5 ppm.

Figure 4A:
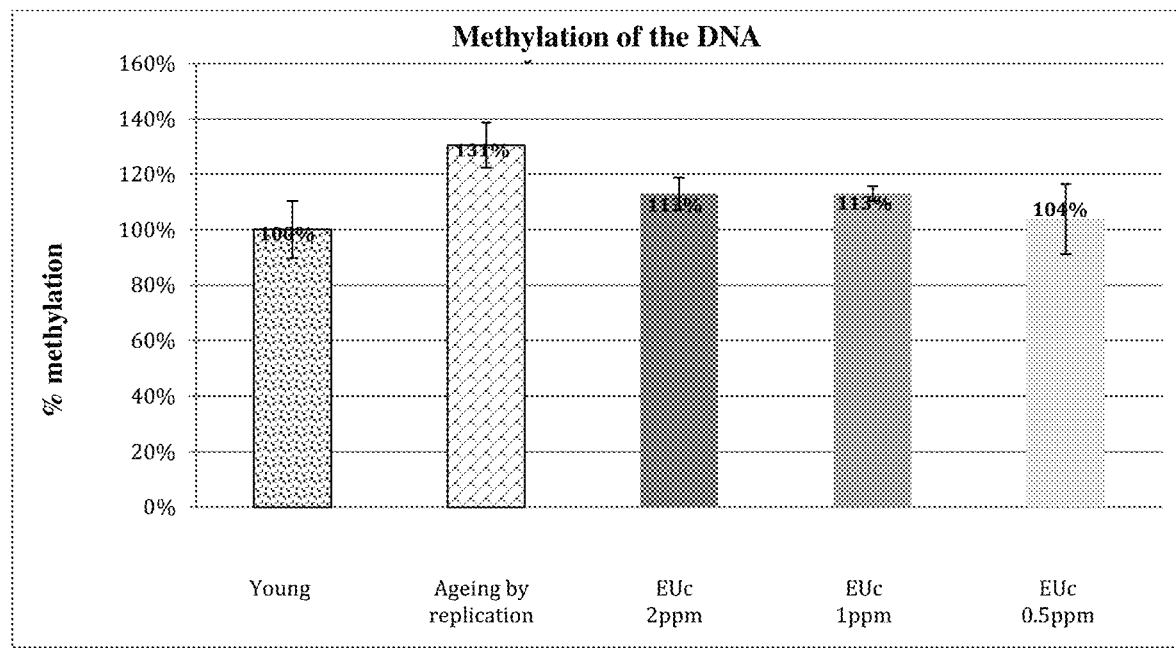

Results: The results are displayed in FIG. 4A.

Conclusion

In view of the results obtained, the Uchuva extract enables to reduce the rate of methylation with three tested concentrations with respect to the aged skin model.

7—Evaluation of the Effect of the Uchuva Extract on the Fibrillin-1 Target

Fibrillin 1 is a protein that constitutes microfibrils, which are associated to elastic fibres and contribute to their assembly.

Study on Young Cells Versus Aged Cells

Method

The young NHDF (Normal Human Dermal Fibroblasts) have been introduced in 96 wells plate and incubated for 24 hours at 37° C., 5% CO2. The cells meant for extrinsic ageing have been irradiated three times with UVA radiation with 24 hours between each irradiation and once with UVB radiation. The cells have been treated in the presence of the test products between each irradiation. Then, the cells have been fixed with formalin and the expression of the proteins has been detected by immunofluorescence. The fluorescent markings have been imaged and quantified by automated microscopy (Arrayscan Cellomics™). The fluorescence has been quantified by the Compartimental Analysis bioapplication.

Cellular Models:
Young: NHDF of young donor (25 years)
UVA/B-induced ageing: NHDF of young donor, irradiated with UVA and UVB radiation Tested Products The Uchuva extract is tested with the following concentrations: 2-1-0.5 ppm following the prior evaluation of its toxicity.

Results

Figure 4B:
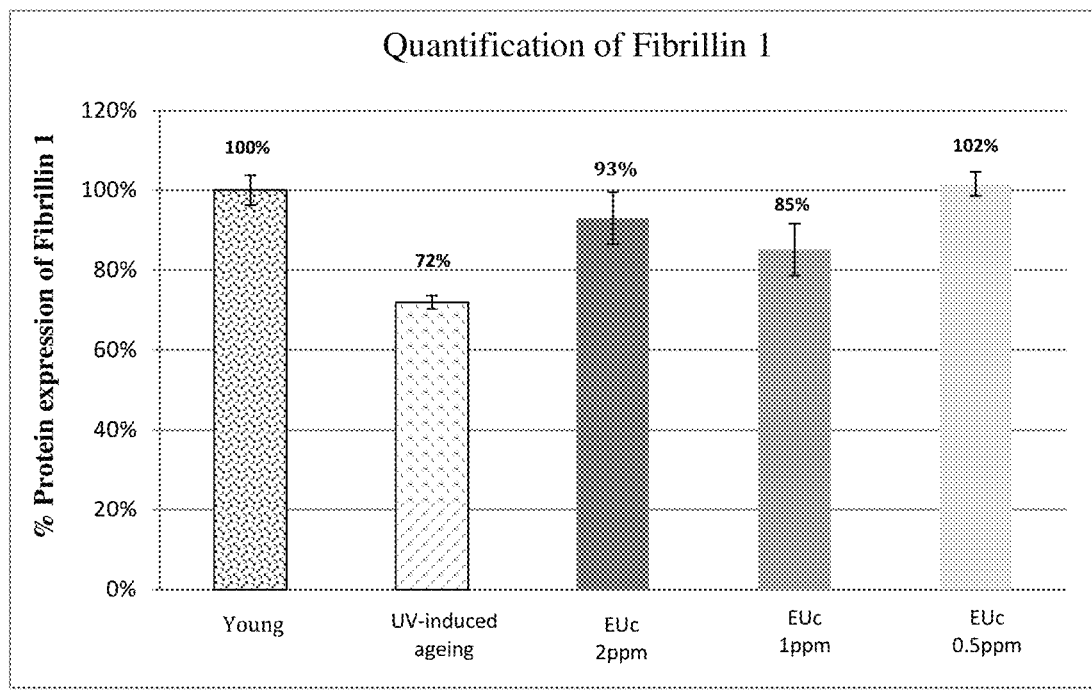

The results are in FIG. 4B.

The Uchuva extract with 0.5 ppm allows re-establishing the expression of Fibrillin 1 to a level that is equivalent, even slightly higher to that of young cells.

General Conclusion about the Anti-Ageing and Rejuvenating Activity

During ageing, the collagen fibres and elastic fibres are altered due to a reduced synthesis and increased degradation. To demonstrate that the Uchuva extract acts on cellular rejuvenation, the expression of the proteins involved in the structure of these fibres in cells aged intrinsically (replicative senescence) in the case of Collagen I and Elastin, or extrinsically by repeated UV radiation (photo-ageing) in the case of Fibrillin 1 have been quantified.

The Uchuva extract allows re-establishing the expression of three markers.

In these studies, the Uchuva extract fully re-establishes the expression of the proteins in comparison with the young control elements. This is the purpose of the observed effects. There is no aberrant overexpression, the Uchuva extract respects the biological balance of the skin.

At the same time, the Uchuva extract also greatly increases the expression of fibroblast Collagen IV with respect to the untreated cells, like Rhamnose recognised for this property. The quantity of Collagen III is also increased during a treatment of fibroblasts by the Uchuva extract. These results reinforce its anti-ageing effectiveness at the redensifying and structural level.

In the context of the analysis of the methylation of the DNA, the Uchuva extract shows homogeneous results in this experiment. It reduces the methylation with three tested concentrations. This effect provides information about the mode of action of this product that enables to reactivate the expression of proteins of the extracellular matrix, giving it its rejuvenating effect.

Therefore, the Uchuva extract is an ingredient or active ingredient exhibiting an anti-ageing, rejuvenating and anti-age biological activity. It consistently acts on three targets of skin ageing by re-establishing the protein expression up to the expression observed in the young cells. It also shows an innovative activity on the epigenetics as is demonstrated by its action on the methylation of the DNA in mature cells. Finally, it shows a deep anti-ageing action by its effectiveness on the synthesis of the proteins of the extracellular matrix.

EXAMPLE 22: TESTS DEMONSTRATING THE MOISTURISING AND STRUCTURING POWER OF THE EPIDERMIS OF THE SKIN BY THE UCHUVA EXTRACT

Filaggrin is synthesised in the stratum granulosum in the form of a precursor, profilaggrin (repetition of 10-12 monomers of filaggrin and the NH2-terminal S-100 regulatory protein). The detection of this protein is associated to a state of terminal differentiation of the epidermis because it appears after dephosphorylation and proteolysis of the profilaggrin that takes place during the terminal differentiation.

1) The filaggrin contributes to the aggregation of keratin during the formation of the packets of macrofibrils,
2) The monomers of filaggrin are components of the cornified layer (CE; envelope that is deposited on the internal surface of the plasma membrane of the corneocytes: contributes to the impermeable properties of the skin with the intercorneocytary lipid matrix),
3) The monomers are completely degraded on the highest layers of the stratum corneum to produce a mixture of hygroscopic amino acids (NMFs or Natural Moisturizing Factors) that are important to maintain the hydration of the epidermis[32].

A decrease in profilaggrin and/or filaggrin has been detected[33] in pathological situations with xerosis or dryness of skin (atopic dermatitis, ichthyosis).

According to Proksch et al[34], the monitoring and expression of filaggrin is a good way to monitor the barrier function and/or the hydration level of the stratum corneum. This is the only real marker that is significant as a hydration marker of the upper layers in the dermatology journals. Nevertheless, clinically, it is a marker that passes after the measurement of the TEWL (TransEpidemal Water Loss).

Involucrin, like filaggrin and loricrin, is a terminal differentiation marker. It is a protein of the cornified envelope (CE) which is the target of the transglutaminases (TGM) and particularly the TGM1. Involucrin is oligomerised by the TGM1 during the initial steps of the formation of the cornified envelope, and for the later steps of the formation of the CE, the involucrin is linked to the ceramides[35]. The marking is localised in the epidermis from the upper layers of the spiny layer till inside the granular layer and the first layers of the SC.

Effect of the Topical Treatment of the Uchuva Extract on Explants of Human Skin

Material and Method:
Description: Explant of human mammal skin from a woman, Caucasian, 51 years old (Biopredic—35000 RENNES).
Number: Preparation of 9 punches of defatted skin with a diameter of 1 cm
Culture conditions: 37° C., 5% CO2
Culture medium: DMEM medium 4.5 g/L of glucose, supplemented and with antibiotics (penicillin-streptomycin-Amphotericin)

Tested Products

The Uchuva extract obtained as per example 3 is diluted to 0.05% and 0.01% (w/v) in paraffin oil. The TRIGLYCERIDES C8C10 55/45 solvent (Code EC-09-271) is used.

Culture Method and Treatment of Explants

The explants are defatted after they are received. Circular skin disks with a diameter of 1 cm have been obtained using a punch. In a six wells plate, a stainless steel grid with a diameter of 1.6 cm is placed in 5 ml of culture medium. Each explant in culture is put on its grid so as to bathe in the culture medium while leaving the epidermis exposed to air. The explants have been cultivated for 48 hours without changing the culture medium. Different treatments have been carried out by a topical administration of 10 μL of the preparations to be tested on D0 and D1. Every experimental condition has been repeated over three punches.

Controlled explants have been cultivated in the same way as the treated explants. The treatments have been carried out by a topical administration of 10 μL of the TRIGLYCER-IDES solvent with the concentration of 0.05%.

Immunolabelling In Situ

After the duration of culture ends, the explants have been collected and then divided into two equal parts using a scalpel. One half has been frozen in tissue Teck™ (Sakura) using isopentane cooled in liquid nitrogen and then maintained at −80° C. awaiting immunolabelling. The second half has been kept in 4% buffered formalin.

5 μm thick cross sections of each explant have been made using a cryotome. The sections have been dried in ambient air. After rehydratation in PBS, the sections have been incubated for 1 hour with the primary antibody solution prepared in a solution (PBS-BSA-Tween). After successive washings, the primary antibodies have been revealed by a secondary antibody connected to an FITC probe at 1/100th of the commercial form. The cell nuclei have been marked by the DAPI fluorescent dye.

The skin sections have been collected using poly-lysine trays.

Microscopic Observations

Each skin section has been observed using an Olympus BX60 epifluorescence microscope with 20× magnification. Two photographs have been taken of each section using an Olympus DP72® camera operated by the Cell F software. The negatives have been identified as follows: Date of marking—Treatment condition—Image number—Marker. The counterstaining of nuclei has been carried out using the DAPI nuclear marker. By sliding colour using the image processing software, the colour of the nuclei has been changed from blue to red. For each treatment condition of the epidermis, there was visual scoring of the intensity of the marking with ×10 magnification. The evaluation scale was as follows:

| | | |
|---|---|---|
| Very low marking | 1 | |
| Low marking | 2 | |
| Moderate marking | 3 | |
| High marking | 4 | |

The data obtained has been analysed, and presented in the form of histograms in comparison with the Triglycerides solvent control conditions.

Results

All the markings were localised at the level of the upper layers of the epidermis (spiny and/or granular and/or cornea of the epidermis).

Filaggrin Immunolabelling

Figure 5A:
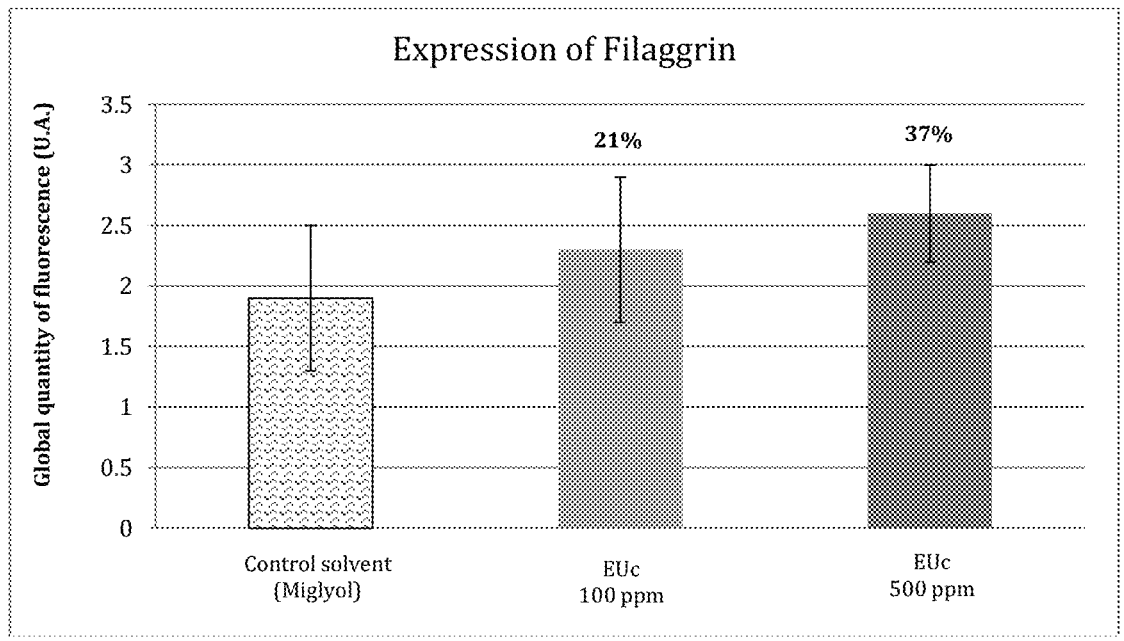

The results of the scoring made are given in the graph of FIG. 5A.

The analysis of the expression data of the Filaggrin marking shows a dose increase dependent on the quantity of fluorescence for the explants treated with the Uchuva extract with 0.01% (+21%) and 0.05% (+37%) in comparison with the Solvent Control group.

Involucrin Immunolabelling

Figure 5B:
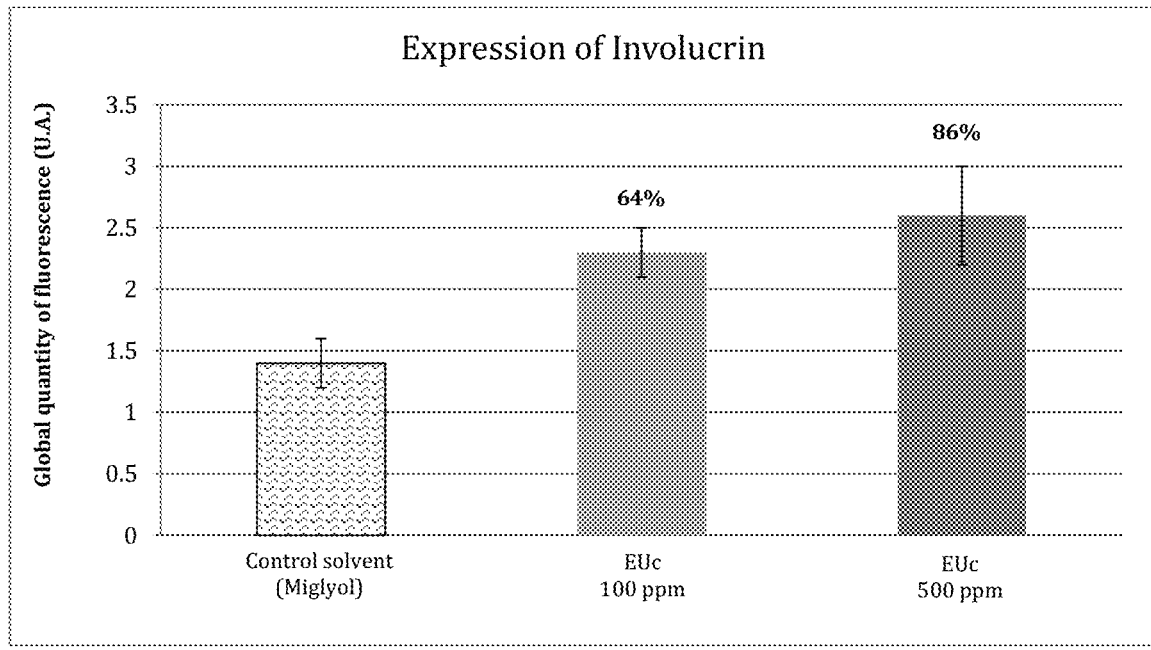

The results of the scoring made are given in the graph of FIG. 5B. The analysis of the expression data of the INVO-LUCRIN marking indicates a significant dose increase dependent on the quantity of fluorescence for the explants treated with the Uchuva extract with 0.01% (+64%) and 0.05% (+86%) in comparison with the Control group.

Conclusion

In this study, the results have shown that the topical treatment of skin explants in culture for 48 hours with the Uchuva extract led to an increase in the expression of proteins involved in hydration and the barrier effect of the skin (filaggrin and involucrin respectively). The increase in expression brought about by the Uchuva extract has been more significant for involucrin than for filaggrin. The maximum expression of these proteins has always been observed with the concentration of 0.05%. According to these results, the Uchuva extract of the invention presents a structuring and moisturising activity profile of the epidermis.

EXAMPLE 23: TESTS DEMONSTRATING THE DEPIGMENTATION POWER OF THE SKIN WITH THE UCHUVA EXTRACT

The depigmentation effect potential of the Uchuva extract has been researched in a model of normal human epidermal melanocytes (NHEM). The effect of the Uchuva extract on the synthesis of melanin has been evaluated after ten incubation days under conditions stimulated by L-tyrosine. In this test, the reference inhibitory molecule is lipoic acid. Its action mechanism calls for an inhibition of the expression of the MITF transcription factor (microphthalmia-associated transcription factor). This transcription factor is the major regulator of the expression of tyrosinase and its inhibition results in the reduction of the expression of tyrosinase, enzyme involved in the melanin synthesis. The melanocytes have been sown in 24 wells plate and cultivated in the culture medium for 24 hours. Then, the medium has been replaced by the culture medium (Medium 254 supplemented with PMA free HMGS-2+Penicillin 50 U/ml—Streptomycin 50 μg/ml) supplemented with L-tyrosine (1 mM) and containing or not containing (stimulated control element) the compound or the reference (lipoic acid tested at 5 μg/ml). A non-stimulated control condition has been created at the same time. Then, the cells have been incubated for a total period of 10 days, with repetitions of the treatments after 3 and 7 days of incubation. After incubation, the melanin has been extracted by lysis of the cells with a solution of NaOH 0.5 N. The optical density (OD) of the samples has been measured at 405 nm, then the quantity of melanin has been determined in comparison with a range of exogenous melanin (melanin curve including standards from 0.39 to 100 μg/ml). The results have been expressed in μg/ml of melanin, in percentage of the stimulated control element and in percentage of inhibition. The treatment of the normal human epidermal melanocytes (NHEM) by L-tyrosine, tested at 1 mM, has strongly stimulated the synthesis of melanin. The reference, lipoic acid, tested at 5 μg/ml, has strongly inhibited the stimulation induced by L-tyrosine (108% inhibition).

This effect was expected and has enabled to validate the test.

The concentrations of the Uchuva extract in the study to be tested have been selected after a preliminary cytotoxicity test:

Cellular type: NHEM in culture medium

Incubation time: 72+96+72 hours

Evaluation parameters: Reduction of the MTT and morphological observations under microscope.

At the end of the treatment, the cells have been incubated in the presence of MTT (tetrazolium salt) whose transformation into blue crystals of formazan is proportional to the activity of the succinate deshydrogenase (mitochondrial enzyme). After dissociation of the cells and solubilisation of the formazan by addition of DMSO, the optical density (OD), which represents the number of living cells and their metabolic activity, has been measured with a 540 nm microplate reader (VERSAmax, Molecular Devices).

Figure 6:
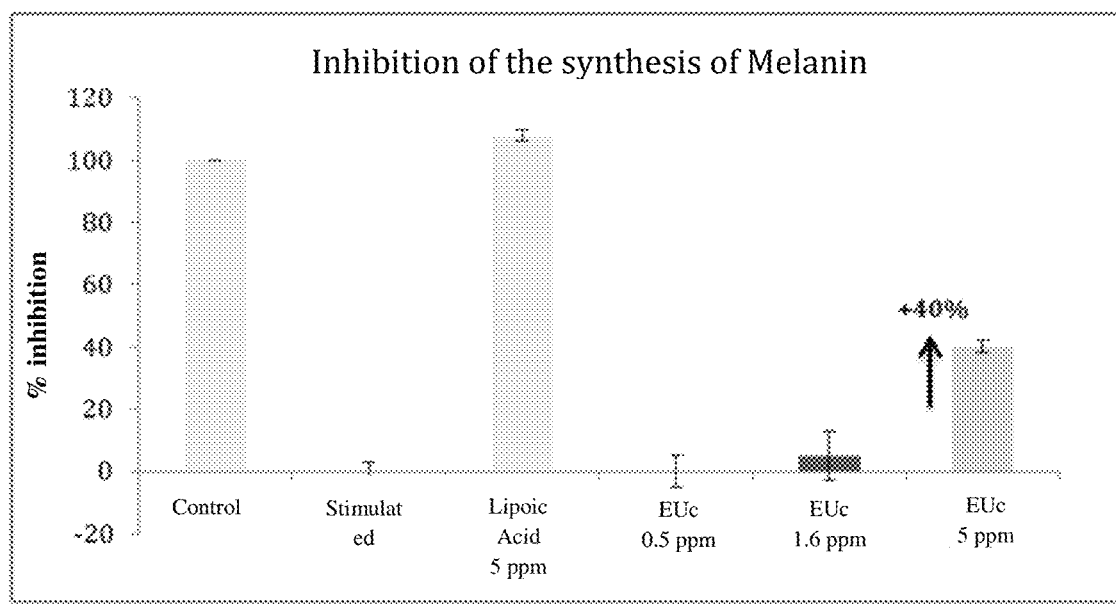

The concentrations thus retained for the rest of the study are: 0.5-1.6-5 µg/ml respectively corresponding to $5 \cdot 10^{-5}$, $16 \cdot 10^{-5}$ and $5 \cdot 10^{-5}\%$. Under experimental conditions of this study, the Uchuva extract, tested at 5 µg/ml, has relatively inhibited the synthesis of melanin (40% inhibition). Tested with lower concentrations, 0.5 and 1.6 µg/ml, the compound showed no effect. The results are given in the diagram in FIG. 6. Under the experimental conditions of this study, the Uchuva extract has shown a moderate depigmentation effect which has been observed only with the strongest tested concentration (5 µg/ml).

The table below shows the correspondence of the concentrations of the Uchuva extract tested in examples 21 to 23 (ppm and % by weight with respect to the total concentration of the composition.

| TARGETS | TESTED CONC. ppm | TESTED CONC. % |
|---|---|---|
| Collagen I | 0.8 | $8 \cdot 10^{-5}$ |
|  | 1.6 | $16 \cdot 10^{-5}$ |
|  | 3.2 | $32 \cdot 10^{-5}$ |
|  | 0.5 | $5 \cdot 10^{-5}$ |
| Collagen I | 1 | $10 \cdot 10^{-5}$ |
|  | 2 | $20 \cdot 10^{-5}$ |
|  | 0.8 | $8 \cdot 10^{-5}$ |
| Collagen III | 1.6 | $16 \cdot 10^{-5}$ |
|  | 3.2 | $32 \cdot 10^{-5}$ |
| Collagen IV | 0.4 | $4 \cdot 10^{-5}$ |
|  | 0.8 | $8 \cdot 10^{-5}$ |
|  | 0.5 | $5 \cdot 10^{-5}$ |
| Elastin | 1 | $10 \cdot 10^{-5}$ |
|  | 2 | $20 \cdot 10^{-5}$ |
|  | 0.5 | $5 \cdot 10^{-5}$ |
| Fibrillin-1 | 1 | $10 \cdot 10^{-5}$ |
|  | 2 | $20 \cdot 10^{-5}$ |
| Methylation Level | 0.5 | $5 \cdot 10^{-5}$ |
|  | 1 | $10 \cdot 10^{-5}$ |
|  | 2 | $20 \cdot 10^{-5}$ |
| Filaggrin | 100 | 0.01 |
|  | 500 | 0.05 |
| Involucrin | 100 | 0.01 |
|  | 500 | 0.05 |
|  | 0.5 | $5 \cdot 10^{-5}$ |
| Melanin | 1.6 | $16 \cdot 10^{-5}$ |
|  | 5 | $50 \cdot 10^{-5}$ |

BIBLIOGRAPHICAL REFERENCES

1. Les esters de sucres: voies de synthèse et potentialités d'utilisation, Piccicuto et al. Biotechnol. Agron. Soc. Environ. 2001, 5, 209-219
2. Domaines d'applications des sucroesters et sucroglycerides, Mireille Cecchin, DESS ingénierie documentaire, rapport bibliographique, 2001.
3. Preparative isolation and structural characterization of sucrose ester isomers from oriental tobacco, Jia et al. Carbohydrate Research 2013, 372, 73-77
4. Characterization of 2,3,4,3'-tetra-O-acylated sucrose esters associated with the glandular trichomes of Lycopersicon typicumKing et al. J. Agric. Food Chem. 1993, 41, 469-473
5. New Multidrug resistance modulators from Atractylodis lanceae RhizomaMurakami et al. Bioorg. Med. Chem. Lett. 2000, 10, 2629-2632
6. Labdanes ans sucrose Ester from Physalis sórdida, Maldonado et al. J. Nat. Prod. 2006, 69, 1511-1513
7. Oligosaccharide esters from the roots of Polygala arillata, Kobayashi et al. J. Nat. Prod. 2000, 63, 1066-1069
8. Synthesis and antitumor activity of lapathoside D and its analogs, Panda et al. Eur. J. Med. Chem. 2012, 53, 1-12
9. Direct inhibition of elastase and matrix metalloproteinases and stimulation of biosynthesis of fibrillar collagens, elastin, and fibrillins by xanthohumol (Journal of Cosmetic Science, Volume 61, Issue 2, Pages 125-132, Journal 2010.)
10. From elastin to elastic fibers, part I. The in vitro effects of a natural dipeptide on the biological cascade.
11. A novel anti-ageing mechanism for retinol: induction of dermal elastin synthesis and elastin fibre formation International Journal of Cosmetic Science Volume 33 Issue 1 Pages 62-69 Journal 2011
12. Matrix proteins of the papillary dermis—primary targets of intrinsic dermal aging? Global Ingredients & Formulations Guide 2009 Pages 131-142 Conference 2009
13. Matrix proteins of the papillary dermis—primary targets of intrinsic dermal aging? IFSCC Magazine Volume 11 Issue 3 Pages 225-229 Journal 2008
14. Fibrillines et fibrillinopathies, Gwenaelle Collod et al., Médecine et Science no 10, vol. 12, p. 1077-1086, octobre 1996
15. Les filaments perés: structure, fonctions et maladies associées, Eric Hanssen et al., Médecine et Science no 3, vol. 17, p. 327-335, mars 2001
16. Stiff skin syndrome cause found, P. J. Couke et al., 18 mars 2010
17. Fibrillin Assembly Requires Fibronectin, L. Sabatier et al., Molecular Biology of the Cell, Vol. 20, 846-858, Feb. 1, 2009.
18. Dissecting the Fibrillin Microfibril: Structural Insights into Organization and Function, S. A. Jensen et al., Structure Review 20, Cell Press, Feb. 8, 2012
19. Type VII collagen gene expression by human skin fibroblasts and keratinocytes in culture: influence of donor age and cytokine responses, Y. K. Chen et al., J Invest Dermatol. 1994 February; 102(2):205-9.
20. WO 2001/007006 A1, ASSOCIATION OF FIBRILLIN AND A CYANOPHYTA EXTRACT, PREPARATION METHOD AND USE AS MEDICINE, PIERRE FABRE DERMO-COSMETIQUE
21. Epidermal growth factor and multiplication of cultured human epidermal keratinocytes, Nature 1977, 265, 421-423
22. Retinoid-Responsive transcriptional changes in epidermal Keratinocytes, Cellular Physiology 2009, 220, 427-439
23. Silybin from Silybum Marianum Seeds inhibits confluent-Induced keratinocytes differentiation as effectively as retinoic acid without inducing inflammatory cytokine, Journal of clinical biochemistry and nutrition, 2009, 45, 178-184.
24. Epigenetic-aging-signature to determine age in different tissues, Carmen M. Koch and Wolfgang Wagner, AGING October 2011, Vol. 3 No 10)
25. Aging is associated with highly defined epigenetic changes in the human epidemis, Raddatz et al. Epigenetics & Chromatin 2013, 6:36
26. Aging, rejuvenation and epigenetic reprogramming—resetting the aging clock, Rando T A, Chang H Y, the Glenn Laboratories for the Biology of Aging, Stanford University School of Medicine, Cell. 2012 Jan. 2; 148(1-2):46-57.doi: 10.1016/j.cell.2012.01.003.
27. Epigenetic control of aging, Muñoz-Najar U., Sedivy J M., Department of Molecula Biology, Cell Biology and Biochemistry, Brown University, Providence, R.I. USA, Antioxid Redox Signal 2011 Jan. 15; 14(2):241-59. Doi: 10.1089/ars.2010.3250. Epub 2010 Nov. 22.
28. Epigenetics and aging, D'Aquila P., Rose G., Bellizzi D., Passarino G., Department of Cell Biology, University of Calabria, Rende Italy, Maturitas 2013 February; 74(2): 130-6. Doi: 10.1016/j.maturitas.2012.11.005. Epub 2012 Dec. 12.
29. Epigenetic factors in aging and longevity, Gravina S., Vijq. J., Department of Genetics, Albert Einstein College of Medicine, Bronx N.Y. USA, Pflugers Arch. 2010 January; 459(2): 247-58. Doi: 10.1007/s00424-009-0730-7. Epub 2009 Sep. 19.
30. Modulation of gene expression as a new skin anti-aging strategy, Talbourdet S., Sadick N S., Lazou K. et co., LVMH Recherche—Parfums Christian Dior, France, J. Drugs Dermatol. 2007 June; 6(6 suppl):s25-33.
31. Experimental approaches to the study of epigenomic dysregulation in ageing, Thompson R F., Fazzari M J., Greally J M., Department of Genetics and Center for Epigenomics, Albert Einstein College of Medicine, Bronx N.Y. USA, Exp. Gerontol. 2010 April; 45(4):225-68. Doi: 10.1016/j.exger.2009.12.013. Epub 2010 Jan. 10.
32. K H Choi et al, Exp Mol Med, 37, 546, 2005.
33. Ginger R S et al., Arch Dermatol Res 297:235-241, 2005; Rawlings A V and Matts P J, JID, 124:1099-1110, 2005.
34. Revue dans Proksch E et al, Exp Dermatol, 17:1063-1072, 2008.
35. Hitomi K. Transglutaminases in skin epidermis, *Eur J Dermatol,* 2005, 15:313.

The invention claimed is:

1. A cosmetic, dermatological or nutracosmetic composition comprising:
   an effective amount of a plant extract from the calyx of one of the many plants of the Solanaceae family, of the *Physalis* genus, comprising mainly one or more moderately polar to non-polar sucrose esters having a carbon number of acyl groups from $C_1$ to $C_{10}$ for use as an active ingredient that is biologically active on skin, skin appendages and mucous membranes apart from any anti-inflammatory activity of the active ingredient, and
   a physiological medium suitable for topical or oral administration,
   wherein the composition is in the form of an oil-in-water or water-in-oil emulsion or multiple emulsions, or in the form of a a capsule, or tablet.

2. The composition according to claim 1, wherein the active ingredient is present at a concentration between $10^{-6}$ and 50% by weight with respect to the total weight of the composition.

3. The composition according to claim 1, wherein the cosmetic composition is in the form of a cream, a lotion, a milk, a shampoo, a serum, an ointment, a gel, a paste, a foam or a stick.

4. A cosmetic treatment process to improve the appearance of skin, mucous membranes or skin appendages, prevent and/or fight against the dryness of skin and mucous membranes, prevent and/or fight against cutaneous signs of ageing, fight against loss of elasticity and firmness of skin and depigment skin, the process comprising: applying on a surface of the skin and/or hair an effective quantity of a topical composition, wherein the topical composition comprises an effective amount of a plant extract from the calyx of one of the many plants of the Solanaceae family, of the *Physalis* genus, comprising mainly one or more moderately polar to non-polar sucrose esters having a carbon number of acyl groups from $C_1$ to $C_{10}$ and wherein the extract is biologically active on skin, skin appendages and mucous membranes apart from any anti-inflammatory activity.

5. A dermatological treatment process for pathological dryness of skin, mucous membranes, hair or skin appendages and to promote healing, comprising: applying to a surface of skin, mucous membranes, hair, or skin appendages and to promote healing, comprising applying to a surface of skin mucous membranes, hair, or skin appendages an effective quantity of a composition, wherein the composition comprises an effective amount of a plant extract from the calyx of one of the many plants of the Solanaceae family, of the *Physalis* genus, comprising mainly one or more moderately polar to non-polar sucrose esters having a carbon number of acyl groups from $C_1$ to $C_{10}$ and wherein the extract is biologically active on skin, skin appendages and mucous membranes apart from any anti-inflammatory activity.

* * * * *